United States Patent [19]
An et al.

[11] Patent Number: 6,156,515
[45] Date of Patent: Dec. 5, 2000

[54] PROSTATE-SPECIFIC GENE FOR DIAGNOSIS, PROGNOSIS AND MANAGEMENT OF PROSTATE CANCER

[75] Inventors: Gang An; Robert Veltri, both of Oklahoma City, Okla.

[73] Assignee: Urocor, Inc., Oklahoma, Okla.

[21] Appl. No.: 09/247,188

[22] Filed: Feb. 9, 1999

[51] Int. Cl.$^7$ .............................. C12Q 1/68; C07H 21/04; C12P 19/34

[52] U.S. Cl. ............................ 435/6; 435/91.2; 435/91.5; 435/91.51; 536/24.31; 536/24.33

[58] Field of Search ............................... 435/6, 91.2, 91.5

[56] References Cited

U.S. PATENT DOCUMENTS

| | | |
|---|---|---|
| 4,196,265 | 4/1980 | Koprowski et al. . |
| 4,215,051 | 7/1980 | Schroeder et al. . |
| 4,683,195 | 7/1987 | Mullis et al. . |
| 4,683,202 | 7/1987 | Mullis . |
| 4,800,159 | 1/1989 | Mullis et al. . |
| 4,883,750 | 11/1989 | Whiteley et al. . |
| 5,262,311 | 11/1993 | Pardee et al. . |
| 5,354,855 | 10/1994 | Cech et al. . |
| 5,359,046 | 10/1994 | Capon et al. . |
| 5,633,161 | 5/1997 | Shyjan . |
| 5,639,656 | 6/1997 | Wright, Jr. . |
| 5,665,547 | 9/1997 | Pardee et al. . |
| 5,882,864 | 3/1999 | An et al. . |

FOREIGN PATENT DOCUMENTS

| | | |
|---|---|---|
| WO 87/00880 | 2/1987 | European Pat. Off. . |
| 0 320308 | 6/1989 | European Pat. Off. . |
| 0 329822 | 8/1989 | European Pat. Off. . |
| 2202328 | 9/1988 | United Kingdom . |
| WO 88/10315 | 12/1988 | WIPO . |
| WO 89/01025 | 2/1989 | WIPO . |
| WO 89/06700 | 7/1989 | WIPO . |
| WO 90/07641 | 12/1990 | WIPO . |
| WO 94/10343 | 5/1994 | WIPO . |

OTHER PUBLICATIONS

Adam and Wright Jr., "Identification of biomarkers in benign: prostate hyperplasia and prostate carcinoma by differential display," *Proceedings*, 86th Annual Meeting American Association for Cancer Research, Mar. 1995.

Alcaraz et al., "Aneupoidy and aneusomy of chromosome 7 detected by fluorescence in situ hybridization are markers of poor prognosis in prostate cancer," *Cancer Res.*, 54:3998–4002, 1994.

An et al., "Differential expression of full–length and trucated Her–2/neu oncogene receptor in prostate cancer assessed using relative quantative RT–PCR," *Molec. Urol.*, 2:305–309, 1998.

An et al., "Isolation of Genes differentially expressed in prostate cancer cells with metastatic potential by arbitrarily–primed differential analyses (ADA)," *Proc. Amer. Assn. Canc. Res.*, 36:82(491), 1995.

An et al., "Identification of novel gene markers in prostate disease by RNA fingerprinting," *Proc. American Assoc. Cancer Res. Annual Mtg*, Abstract No. 1692 37(0):248, 1996.

An et al., "Sensitive, nonradioactive differential display method using chemiluminescent detection," *Biotechniques*, 20(3):342, 344, 346, 1996.

Badalament et al., "An algorithm for predicting nonorgan confined prostate cancer using the results obtained from sextant core biopsies with prostate specific antigen level," *J. Urol.*, 156:1375–1380, 1996.

Blok et al., "Isolation of cDNAs that are differentially expressed between androgen–dependent and androgen–independent prostate carcinoma cells using differential display PCR$^{TM}$," *Prostate*, 26(4):213–224, 1995.

Bookstein et al., "Promoter deletion and loss of retinoblastoma gene expression in human prostate carcinoma," *Proc. Natl. Acad. Sci. USA*, 87:7762–7766, 1990.

Bookstein et al., "Suppression of tumorigenicity of human prostate carcinoma cells by replacing a mutated RB gene," *Science*, 247:712–715, 1990.

Bova et al., "Homozygous deletion and frequent allelic loss of chromosome 8p22 loci in human prostate cancer," *Cancer Res.*, 53:3869–3873, 1993.

Bussemakers et al., "Identifiication of high mobility group protein I(Y) as potential progression marker for prostate cancer by differential hybridization analysis," *Cancer Res.*, 51:606–611, 1991.

Carter et al., "Allelic loss of chromosomes 16q and 10q in human prostate cancer," *Proc. Natl. Acad. Sci. USA*, 87:8751–8755, 1990.

Chen et al., "Androgen–independent human prostate cancer progression: the isolation of novel stage–specific sequences using differential mRNA display," *Proc. Natl. Urol. Assn.*, 153:267A, 1995.

Deguchi et al., "Detection of micrometastatic prostate cancer cells in lymph nodes by reverse transcriptase–polymerase chain reaction," *Cancer Research*, 53:5350–5354, 1993.

Dong et al, "KAI1, a metastasis suppressor gene for prostate cancer on human chromosome 11p11.2,"*Science*, 268:884–886, 1995.

Donohue et al., "A delayed–early gene activated by fibroblast growth factor–1 encodes a protein related to aldose reductase," *J. Biol. Chem.*, 269(11):8604–8609, 1994.

(List continued on next page.)

*Primary Examiner*—Eggerton A. Campbell
*Assistant Examiner*—Anna B. Pawul
*Attorney, Agent, or Firm*—Fulbright & Jaworski

[57] ABSTRACT

Disclosed are nucleic acid and amino acid sequences encoded by a novel, prostate specific gene (UC41) and diagnostic techniques for the detection of human prostate cancer utilizing such nucleic acid and amino acid sequences. Genetic probes and methods useful in monitoring the progression and diagnosis of prostate cancer are described. Methods of treatment for prostate cancer utilizing antisense constructs or antibodies specific for UC41 gene products are also described.

14 Claims, 10 Drawing Sheets

(4 of 10 Drawing Sheet(s) Filed in Color)

OTHER PUBLICATIONS

Dubensky et al., "Direct transfection of viral and plasmid DNA into the liver or spleen of mice," *Proc. Nat. Acad. Sci. USA*, 81:7529–7533, 1984.

Dumont et al., "Relationship between multiple biologic effects of rapamycin and the inhibition of pp70S6 protein kinase activity," *J. Immunology*, 992–1003, 1994.

EMBL. Sequence Data Library, Heidelberg, BRD, XP002019347, Accession No. W67972.

Garcia–Arenas et al., "The expression of prostatic acid phosphatase in transcriptionally regulated in human prostate carcinoma cells," *Mol. Cell. Endocrin.*, 111:29–37, 1995.

Gomella et al., "RT–PCR for prostate specific antigen in the management of prostate cancer," *J. Urol.*, 158:326–327, 1997.

Hamdy et al., "Circulating prostate specific antigen–positive cells correlate with metastatic prostate cancer," *Brit. J. Urology*, 69(4):392–396, 1992.

Isaacs et al., "Molecular biology of prostate cancer," *Seminars in Oncology*, 21(5):514–521, 1994.

Isaacs et al., "Wild–type p53 suppresses growth of human prostate cancer cells containing mutant p53 Alleles," *Cancer Res.*, 51:4716–4720, 1991.

Kawasaki and Wang, "Detection of gene expression," *In: PCR Technology*, Henry A. Erlich (ed.), Stockton Press, 1989.

Liang et al., "Differential display and cloning of messenger RNAs from human breast cancer versus mammary epithelial cells," *Cancer Res.*, 52:6966–6968, 1992.

Liang and Pardee, "Differential display of eukaryotic messenger RNA by means of the polymerase chain reaction," *Science*, 257:967–971, 1992.

Lithrup et al, Cost–effective prostate cancer detection. Reduction of low–yield biopsies. Investigators of the American Cancer Society National Prostate Cancer Detection Project. *Cancer*, Dec. 15;74(12):3146–58, 1994.

Macoska et al., "Fluorescence in Situ hybridization analysis of 8p allelic loss and chromosome 8 instability in human prostate cancer," *Cancer Research*, 54:3824–3830, 1994.

Mok et al., "Molecular cloning of differentially expressed genes in human epithelial ovarian cancer," *Gynecological Oncology*, 52:247–252, 1994.

Morton et al., "Multivariate analysis of the relationship between survival and the microstage of primary melanoma by clark level and breslow thickness," *Cancer*, 71(11):3737–3743, 1993.

Morton et al., "Reduction of E–cadherin levels and deletion of the α–catenin gene in human prostate cancer cells," *Cancer Research*, 53:3585–3590, 1993.

O'Dowd et al., "Update on the appropriate staging evaluation for newly diagnosed prostate cancer," *J. Urol.*, 158:687–698, 1997.

Olsson et al., "RT–PCR assays for prostate cancer," *Urol. Clinics of North America .*, 24(2):367–378, 1997.

Orozco et al., "Observations on pathology trends in 62,537 prostate biopsies obtained from urology private practices in the United States," *Urology*, 51(2):186–195, 1998.

Partin and Oesterling, "The clinical usefulness of prostate specific antigen: update," *J. Urol.*, 152:1358–1368, 1994.

PCT Search Report mailed Feb. 7, 1997.

Piironen et al, "Immunofluorometric assay for sensitive and specific measurement of human prostatic glandular kallikrein (hK2) in serum,"*Clin. Chem.* 42:1034–1041, 1996.

Prashar et al., "Analysis of differential gene expression by display of 3' end restriction fragments of cDNAs," *Proc. Natl. Acad. Sci. USA*, 93:569–663, 1996.

Qiao et al., "Effects of suramin on expression of proliferation associated nuclear antigens in DU–145 prostate carcinoma cells," *Biochemical and Biophysical Research Communications*, 201(2):581–588, 1994.

Ribas de Pouplana and Fothergill–Gilmore, "The active site architecture of a short–chain dehydrogenase defined by site–directed mutagenesis and structure modeling." *Biochemistry*, 33:7047–7055, 1994.

Riber, Manuel, Rieber, "Cyclin–dependent kinase 2 and cyclin A interaction with E2F are targets for tyrosine induction of B16 melanoma terminal differentiation," *Cell Growth and Differentiation*, 5:1339–1346, 1994.

Robson et al., "Identification of prostatic androgen regulated genes using the differential display technique," *Proc. American Assoc. Cancer Research Annual Meeting*, Abstract No. 1589. 36:266, 1995.

Sager et al., "Identification by differential display of alpha–6 integrin as a candidate tumor suppressor gene," *Methodology Communications*, 7:964–970, Jul., 1993.

Scott et al., "A truncated intracellular HER2/neu receptor produced by alternative RNA processing affects growth of human carcinoma cells," *Molecular and Cellular Biology*, 13(4):2247–2257, 1993.

Slamon et al., "Expression of cellular oncogenes in human malignancies," *Science*, 224:256–262, 1984.

Sun and Cohen, "Computer–assisted drug discovery—a review". *Gene*, 137:127–132, 1993.

Takahashi et al., "Potential markers of prostate cancer aggressiveness detected by fluorescence in Situ hybridization in needle biopsies," *Cancer Research*, 54:3574–3579, 1994.

Umbas et al., "Expression of the cellular adhesion molecule E–cadherin is reduced or absent in high–grade prostate cancer," *Cancer Research*, 52:5104–5109, 1992.

Umbas et al., "Relation between aberrant alpha–catenin expression and loss of E–cadherin function in prostate cancer," *Int. J. Cancer (Pred. Oncol.)*, 74:374–377, 1997.

Veltri et al, "Quantitative nuclear morphometry, Markovian texture descriptors, and DNA content captured on a CAS–200 Image analysis system, combined with PCNA and HER–2/neu immunohistochemistry for predictions of prostate cancer progression." *J. Cell Biochem*, 19(suppl):249–258, 1994.

Veltri et al., "Ability to predict biochemical progression using gleason score and a computer–generated quantitative nuclear grade derived from cancer cell nuclei," *Urology*, 48(5):685–691, 1996.

Veltri et al., "The role of biopsy pathology, quantitative nuclear morphometry, and biomarkers in the preoperative prediction of prostate cancer staging and prognosis," *Seminars in Urologic Oncology*, 16(3):106–117, 1998.

Veltri et al., "Interleukin–8 serum levels in patients with benign prostatic hyperplasia and prostate cancer," *Urology*, 53(1):139–147, 1999.

Visakorpi et al. "Sensitive detection of chromosome copy number abberations in prostate cancer by fluorescence In Situ hybridization," *J. Pathology*, 145(3):624–630, 1994.

Wagner et al, "Antisense gene inhibition by oligonucleotides containing C–5 propyne pyrimidines".*Science*, 260:1510–1513, 1993.

Watson and Fleming, "Isolation of differentially expressed sequence tags from human breast cancer," *Cancer Research*, 54:4598–4602, 1994.

Webb and Lin, "Urinary fibronectin–potential as a biomarker in prostatic cancer," *Investigative Urology*, 17(5)401–404, 1980.

Welsh et al., "Arbitrarily primed PCR fingerprinting of RNA," *Nucleic Acids Research*, 20(19):4965–4970, 1992.

Wingo et al., "An adjustment to the 1997 estimate for new prostate cancer cases," *CA–A Cancer Journal for Clinicians*, 47(4):239–242, 1997.

Wong et al., "Identification of differentially expressed RNA in human ovarian carcinoma cells by arbitrarily primed PCR fingerprinting of total RNAs," *Intl. J. Onc.*, 3:13–17, 1993.

| A1 Whole Brain | A2 Amygdala | A3 Caudate Nucleus | A4 Cerebellum | A5 Cerebral Cortex | A6 Frontal Lobe | A7 Hippo-campus | A8 Medulla Oblongata |
|---|---|---|---|---|---|---|---|
| B1 Occipital Lobe | B2 Putamen | B3 Substantia Nigra | B4 Temporal Lobe | B5 Thalamus | B6 Acumens | B7 Spinal Cord | B8 |
| C1 Heart | C2 Aorta | C3 Skeletal Muscle | C4 Colon | C5 Bladder | C6 Uterus | C7 Prostate | C8 Stomach |
| D1 Testis | D2 Ovary | D3 Pancreas | D4 Pituitary Gland | D5 Adrenal Gland | D6 Thyroid Gland | D7 Salivary Gland | D8 Mammary Gland |
| E1 Kidney | E2 Liver | E3 Small Intestine | E4 Spleen | E5 Thymus | E6 Peripheral Leukocyte | E7 Lymph Node | E8 Bone Marrow |
| F1 Appendix | F2 Lung | F3 Trachea | F4 Placenta | F5 | F6 | F7 | F8 |
| G1 Fetal Brain | G2 Fetal Heart | G3 Fetal Kidney | G4 Fetal Liver | G5 Fetal Spleen | G6 Fetal Thymus | G7 Fetal Lung | G8 |
| H1 Yeast Total RNA | H2 Yeast tRNA | H3 E coli rRNA | H4 E coli DNA | H5 Poly r(A) | H6 Human $C_{ot}1$ DNA | H7 Human DNA | H8 Human DNA |

FIG. 7

 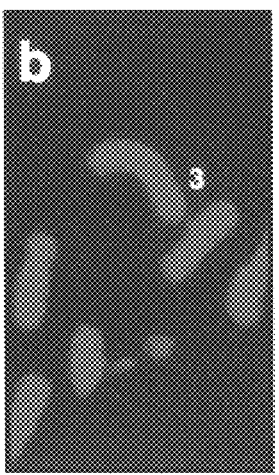 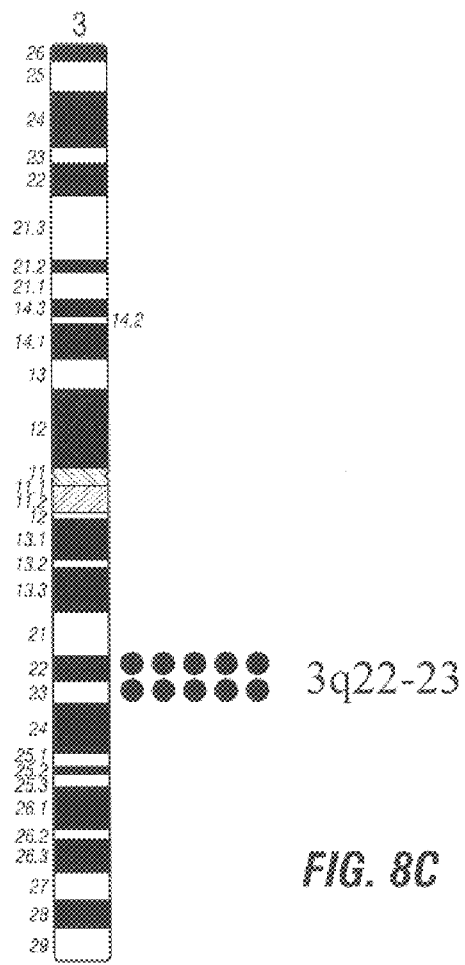
FIG. 8A  FIG. 8B
FIG. 8C

```
1     ATAAATACTCACACTTTCAAAGTAAACGCTCTTCTTTTCTATGTGCTCCA
51    TATCGCTTTGCCCTCTTTATTTGAGCAACGTACCCTGTAGTGTGTAAATA
101   AGAGATGACAGCTCCTATAATACGTGTGGGTGAGGAATGGGTTCGATAAA
151   ACAGAAGCATGCACAATTCAAATAGCAAGCCCTGTCCCACTCAGTTTATG
201   CACAAATAACTTGCAGATTCTCTGATTTTCTGCCAGCAACTGCCTCCTCT
251   TCCCCTCCCCACTGCCTTCCAGAAGTCTCTCAGAATCATATCCGGCACGG
301   TGTATAGAGATAGGAGTAATAGGGATAAGACTTGTTTTTTCTGAATTTTA
351   ATTATTGTCATTTAGCATTTGCTCAGTGTTTTGTGATGAAAATCGTTGGG
401   TTTTACTTATTTTTACTATGGGCAAATTGAGATGCCTTTAATCATAAAGG
451   CAGCCCCAACCCAAGGTACCCTTGCATAATAGCGGAAGGGGTGAGATTAG
501   GAGTAAGCCTTTAGAGCACCGGTGCAGGACTCAGGATATGGATTTGTGGC
551   TTGTTCTTATATGCCGTATTTGTCTTATGGGTAAATGCTGTATATCGTTT
601   TGATTTTTCCTATCGTGGAACACTTTTCAGTTATATGTCTGGTGGAATCA
651   AGTGTTTCATGTTACTTTTAAATGTACATAGGTGGCTTAATTTTTTTTAT
701   TTACAATTCAGCACTTCAGATGTGAAGAGATATGGCTTTTTCTTTTTTTT
751   TTTTTTACAACAGAATATAACTTGCTTCTGAGCCCTCATTTCTGATTGG
801   TGGTGATGGAAACCTTAGCTTGCCTGTTGGAGGTAACTGTCACTTCCAAT
851   TCACTGCAGTCTTGTCCAGGTTAACACAATCATGTTGGTGTAAATAGTCA
901   ACTGAGGATTTAAATAGTCAATTCAAAATGCAAACTTCTTATCTAAGTGA
951   TTCTCCCCTCTCAAGGAATTTCCCCTTCCTGTCCTCTTTCCAGTATGTTA
1001  TCTGGGTTCAGAGTGGGTACTTGTATAACTACACAACACAGAGGAAGAGA
1051  GTCCAGTTCTCATGCAGTCATCTGGATCCCTGCTGGCCACCTCTGAAGTA
1101  GATGTCTATATCCACTGTGCTAAGTGGTCTTCCAATGGATCCAGTTGGT
1151  CATTAGTGGAGCTCTAGAACCTGCTGATGATTCATGGTCCCTGCCAACTT
1201  CCTCTCTATGCCCTCCTCATTCAAAGTGAAGGTTTCTTTCAGCTTATTGG
1251  CCCTTTGGCCCATTCCCATTCTTTGTAGAAACTTCTGCAGACCACATTCA
```

*FIG. 9A*

1301 GCCACTGGAAAACCAAAATATGCTTTCTCATCTCTCTCCTCTCCTTCACG
1351 ATGCCATTCTGCCATTTCTGTTTTGTGGTAGACAGGTTGGCCCAGGCACT
1401 CTAAGGCCCAGGCTGGCACAGGTTGGCCCAGGCACTTCAAGCCTAAGTCC
1451 ATTTACAGTTTCTATTCCATCTATTCCTAAAGAAGGAGGCAGAGGGCAGG
1501 TCTCAACTCGTGTTTCAGCACTGCTGTTTTACACACACACACACACCCTC
1551 TCTCCAGGCATCTCTAACTCAGGCAGAACTTTTATTTCCTCCCAATATGG
1601 CAGAAACCACCTTCAATTTCATATCAGGATATTTCCTTCTTTATTGTTTA
1651 TAGTTTACTTTGCAACTGAGGTGATCTCCAAAGAGGCTGATAGATGAGGA
1701 CTAATTGCTAACTGCACTCCCAGCTGCAACAGGCATGAAGGAAGATATGG
1751 GTGGTCCATCTCCATGTTCATTACAGTGATAGGTCAGCTGTCTCCAACCT
1801 TTTTGGCATCAGGGACTAGTTTTGTGGAGACAATTTTTCCATGGACATG
1851 GGGTGGGGAAGGAAGGAGATGATTTTGGGTTGAAACTGTTCCACTTCAGA
1901 CTCAGATCATCAGGCGTTAGATTATCATAAGGAC (SEQ ID NO:1)

*** start site ^^^ stop site
▭ leading signal
— transmembrane domain

FIG. 9B

SEQUENCE LISTING

<160> NUMBER OF SEQ ID NOS: 15

<210> SEQ ID NO 1
<211> LENGTH: 1934
<212> TYPE: DNA
<213> ORGANISM: Homo sapiens

<400> SEQUENCE: 1

-continued

```
ataaatactc acactttcaa agtaaacgct cttcttttct atgtgctcca tatcgctttg      60
ccctctttat ttgagcaacg taccctgtag tgtgtaaata agagatgaca gctcctataa     120
tacgtgtggg tgaggaatgg gttcgataaa acagaagcat gcacaattca aatagcaagc     180
cctgtcccac tcagtttatg cacaaataac ttgcagattc tctgatttc  tgccagcaac     240 tgcctcctct tcccctcccc actgccttcc agaagtctct cagaatcata tccggcacgg     300
tgtatagaga taggagtaat agggataaga cttgtttttt ctgaatttta attattgtca     360
tttagcattt gctcagtgtt ttgtgatgaa atcgttggg  ttttacttat ttttactatg     420
ggcaaattga gatgccttta atcataaagg cagccccaac ccaaggtacc cttgcataat     480
agcggaaggg gtgagattag gagtaagcct ttagagcacc ggtgcaggac tcaggatatg     540
gatttgtggc ttgttcttat atgccgtatt tgtcttatgg gtaaatgctg tatatcgttt     600 tgattttcc  tatcgtggaa cacttttcag ttatatgtct ggtggaatca agtgtttcat     660 gttacttta  aatgtacata ggtggcttaa ttttttttat ttacaattca gcacttcaga     720
tgtgaagaga tatggctttt tcttttttt  ttttttttaca acagaatata acttgcttct     780
gagccctcat ttctgattgg tggtgatgga aaccttagct tgcctgttgg aggtaactgt     840
cacttccaat tcactgcagt cttgtccagg ttaacacaat catgttggtg taaatagtca     900
actgaggatt taaatagtca attcaaaatg caaacttctt atctaagtga ttctcccctc     960
tcaaggaatt tccccttcct gtcctctttc cagtatgtta tctgggttca gagtgggtac    1020
ttgtataact acacaacaca gaggaagaga gtccagttct catgcagtca tctggatccc    1080
tgctggccac ctctgaagta gatgtctata tccactgtgc taagtggtct tggaaatgga    1140
tccagttggt cattagtgga gctctagaac ctgctgatga ttcatggtcc ctgccaactt    1200
cctctctatg ccctcctcat tcaaagtgaa ggtttctttc agcttattgg cccctttggcc    1260 cattcccatt ctttgtagaa acttctgcag accacattca gccactggaa aaccaaaata    1320
tgctttctca tctctctcct ctccttcacg atgccattct gccatttctg ttttgtggta    1380
gacaggttgg cccaggcact ctaaggccca ggctggcaca ggttggccca ggcacttcaa    1440
gcctaagtcc atttacagtt tctattccat ctattcctaa agaaggaggc agagggcagg    1500
tctcaactcg tgtttcagca ctgctgtttt acacacacac acacccctc  tctccaggca    1560 tctctaactc aggcagaact tttatttcct cccaatatgg cagaaaccac cttcaatttc    1620
atatcaggat atttccttct ttattgttta tagtttactt tgcaactgag gtgatctcca    1680
aagaggctga tagatgagga ctaattgcta actgcactcc cagctgcaac aggcatgaag    1740
gaagatatgt gtggtccatc tccatgttca ttacagtgat aggtcagctg tctccaacct    1800
ttttggcatc agggactagt tttgtggaag acaattttc  catggacatg gggtggggaa    1860
ggaaggagat gattttgggt tgaaactgtt ccacttcaga ctcagatcat caggcgttag    1920
attatcataa ggac                                                     1934
```

<210> SEQ ID NO 2
<211> LENGTH: 125
<212> TYPE: PRT
<213> ORGANISM: Homo sapiens

<400> SEQUENCE: 2

```
Met Leu Ser His Leu Ser Pro Leu Leu His Asp Ala Ile Leu Pro Phe
 1               5                  10                  15

Leu Phe Cys Gly Arg Gln Val Gly Pro Gly Thr Leu Arg Pro Arg Leu
            20                  25                  30
```

Ala Gln Val Gly Pro Gly Thr Ser Ser Leu Ser Pro Phe Thr Val Ser
          35                  40                  45

Ile Pro Ser Ile Pro Lys Glu Gly Arg Gly Gln Val Ser Thr Arg
 50                  55                  60

Val Ser Ala Leu Leu Phe Tyr Thr His Thr His Thr Leu Ser Pro Gly
 65                  70                  75                  80

Ile Ser Asn Ser Gly Arg Thr Phe Ile Ser Ser Gln Tyr Gly Arg Asn
                 85                  90                  95

His Leu Gln Phe His Ile Arg Ile Phe Pro Ser Leu Leu Phe Ile Val
             100                 105                 110

Tyr Phe Ala Thr Glu Val Ile Ser Lys Glu Ala Asp Arg
         115                 120                 125

<210> SEQ ID NO 3
<211> LENGTH: 1322
<212> TYPE: DNA
<213> ORGANISM: Homo sapiens

<400> SEQUENCE: 3
ataaatactc acactttcaa agtaaacgct cttcttttct atgtgctcca tatcgctttg      60
ccctctttat ttgagcaacg taccctgtag tgtgtaaata agagatgaca gctcctataa     120
tacgtgtggg tgaggaatgg gttcgataaa acagaagcat gcacaattca aatagcaagc     180
cctgtcccac tcagtttatg cacaaataac ttgcagattc tctgattttc tgccagcaac     240
tgcctcctct tcccctcccc actgccttcc agaagtctct cagaatcata tccggcacgg     300
tgtatagaga taggagtaat agggataaga cttgtttttt ctgaattta attattgtca      360 tttagcattt gctcagtgtt ttgtgatgaa aatcgttggg ttttacttat ttttactatg     420
ggcaaattga gatgccttta atcataaagg cagccccaac ccaaggtacc cttgcataat     480
agcggaaggg gtgagattag gagtaagcct ttagagcacc ggtgcaggac tcaggatatg     540
gatttgtggc ttgttcttat atgccgtatt tgtcttatgg gtaaatgctg tatatcgttt     600 tgattttttcc tatcgtggaa cacttttcag ttatatgtct ggtggaatca agtgtttcat     660
gttactttta aatgtacata ggtggcttaa ttttttttat ttacaattca gcacttcaga     720
tgtgaagaga tatggctttt tctttttttt tttttttaca acagaatata acttgcttct     780
gagccctcat ttctgattgg tggtgatgga aaccttagct tgcctgttgg aggtaactgt     840
cacttccaat tcactgcagt cttgtccagg ttaacacaat catgttggtg taaatagtca     900
actgaggatt taaatagtca attcaaaatg caaacttctt atctaagtga ttctcccctc     960
tcaaggaatt tccccttcct gtcctctttc cagtatgtta tctgggttca gagtgggtac    1020
ttgtataact acacaacaca gaggaagaga gtccagttct catgcagtca tctggatccc    1080
tgctggccac ctctgaagta gatgtctata tccactgtgc taagtggtct tggaaatgga    1140
tccagttggt cattagtgga gctctagaac ctgctgatga ttcatggtcc ctgccaactt    1200
cctctctatg ccctcctcat tcaaagtgaa ggtttctttc agcttattgg ccctttggcc    1260
cattcccatt ctttgtagaa acttctgcag accacattca gccactggaa aaccaaaata    1320
tg                                                                    1322

<210> SEQ ID NO 4
<211> LENGTH: 434
<212> TYPE: DNA
<213> ORGANISM: Homo sapiens -continued

```
<400> SEQUENCE: 4
tctcaactcg tgtttcagca ctgctgtttt acacacacac acacaccctc tctccaggca      60
tctctaactc aggcagaact tttatttcct cccaatatgg cagaaaccac cttcaatttc     120
atatcaggat atttccttct ttattgttta tagtttactt tgcaactgag gtgatctcca     180
aagaggctga tagatgagga ctaattgcta actgcactcc cagctgcaac aggcatgaag     240
gaagatatgg gtggtccatc tccatgttca ttacagtgat aggtcagctg tctccaacct     300
ttttggcatc agggactagt tttgtggaag acaatttttc catggacatg ggtgggggaa     360
ggaaggagat gattttgggt tgaaactgtt ccacttcaga ctcagatcat caggcgttag     420
attatcataa ggac                                                       434

<210> SEQ ID NO 5
<211> LENGTH: 65
<212> TYPE: PRT
<213> ORGANISM: Homo sapiens

<400> SEQUENCE: 5

Val Ser Thr Arg Val Ser Ala Leu Leu Phe Tyr Thr His Thr His Thr
 1               5                  10                  15

Leu Ser Pro Gly Ile Ser Asn Ser Gly Arg Thr Phe Ile Ser Ser Gln
            20                  25                  30

Tyr Gly Arg Asn His Leu Gln Phe His Ile Arg Ile Phe Pro Ser Leu
        35                  40                  45

Leu Phe Ile Val Tyr Phe Ala Thr Glu Val Ile Ser Lys Glu Ala Asp
    50                  55                  60

Arg
 65

<210> SEQ ID NO 6
<211> LENGTH: 10
<212> TYPE: DNA
<213> ORGANISM: Homo sapiens

<400> SEQUENCE: 6
ctagtgatta                                                             10

<210> SEQ ID NO 7
<211> LENGTH: 10
<212> TYPE: DNA
<213> ORGANISM: Homo sapiens

<400> SEQUENCE: 7
gtccttatga                                                             10

<210> SEQ ID NO 8
<211> LENGTH: 29
<212> TYPE: DNA
<213> ORGANISM: Homo sapiens

<400> SEQUENCE: 8
aaaacgatat catgctttct catctctcc                                        29

<210> SEQ ID NO 9
<211> LENGTH: 32
<212> TYPE: DNA
<213> ORGANISM: Homo sapiens

<400> SEQUENCE: 9
```

-continued

```
caattgcggc cgctctatca gcctctttgg ag                    32

<210> SEQ ID NO 10
<211> LENGTH: 24
<212> TYPE: DNA
<213> ORGANISM: Homo sapiens

<400> SEQUENCE: 10
caaatagcaa gccctgccca ctca                             24

<210> SEQ ID NO 11
<211> LENGTH: 25
<212> TYPE: DNA
<213> ORGANISM: Homo sapiens

<400> SEQUENCE: 11
ctcctaatct caccccttcc gctat                            25

<210> SEQ ID NO 12
<211> LENGTH: 28
<212> TYPE: DNA
<213> ORGANISM: Homo sapiens

<400> SEQUENCE: 12
cacgtcatcc agcagagaat ggaaagtc                         28

<210> SEQ ID NO 13
<211> LENGTH: 28
<212> TYPE: DNA
<213> ORGANISM: Homo sapiens

<400> SEQUENCE: 13
gagaataggt tgtagttgta gaaccagt                         28

<210> SEQ ID NO 14
<211> LENGTH: 21
<212> TYPE: DNA
<213> ORGANISM: Homo sapiens

<400> SEQUENCE: 14
ctgccaactt cctctctatg c                                21

<210> SEQ ID NO 15
<211> LENGTH: 23
<212> TYPE: DNA
<213> ORGANISM: Homo sapiens

<400> SEQUENCE: 15
gtcctcatct atcagcctct ttg                              23
```

PROSTATE-SPECIFIC GENE FOR DIAGNOSIS, PROGNOSIS AND MANAGEMENT OF PROSTATE CANCER

BACKGROUND OF THE INVENTION

1.1 Field of the Invention

The present invention relates generally to novel nucleic acid sequences, polypeptides encoded by the novel nucleic acid sequences and antibodies specific for such polypeptides, useful as probes or primers for the diagnosis, prognosis and management of prostate cancer and methods relating thereto. More particularly, the present invention concerns probes, primers and methods useful in diagnosing, identifying and monitoring the progression of prostate cancer through measurements of gene products. The present invention also concerns a novel prostate specific gene and methods of treatment for prostate cancer, based upon the disclosed nucleic acid and polypeptide sequences.

1.2 Description of the Related Art

Genetic detection of human disease states is a rapidly developing field (Taparowsky et al., 1982; Slamon et al., 1989; Sidransky et al., 1992; Miki et al., 1994; Dong et al., 1995; Morahan et al., 1996; Lifton, 1996; Barinaga, 1996). However, some problems exist with this approach. A number of known genetic lesions merely predispose to development of specific disease states. Individuals carrying the genetic lesion may not develop the disease state, while other individuals may develop the disease state without possessing a particular genetic lesion. In human cancers, genetic defects may potentially occur in a large number of known tumor suppresser genes and proto-oncogenes.

The genetic detection of cancer has a long history. One of the earliest genetic lesions shown to predispose to cancer was transforming point mutations in the ras oncogenes (Taparowsky et al., 1982). Transforming ras point mutations may be detected in the stool of individuals with benign and malignant colorectal tumors (Sidransky et al., 1992). However, only 50% of such tumors contained a ras mutation (Sidransky et al., 1992). Similar results have been obtained with amplification of HER-2/neu in breast and ovarian cancer (Slamon et al., 1989), deletion and mutation of p53 in bladder cancer (Sidransky et al., 1991), deletion of DCC in colorectal cancer (Fearon et al., 1990) and mutation of BRCA1 in breast and ovarian cancer (Miki et al., 1994).

None of these genetic lesions are capable of predicting a majority of individuals with cancer and most require direct sampling of a suspected tumor, making screening difficult.

Further, none of the markers described above are capable of distinguishing between metastatic and non-metastatic forms of cancer. In effective management of cancer patients, identification of those individuals whose tumors have already metastasized or are likely to metastasize is critical. Because metastatic cancer kills 560,000 people in the U.S. each year (ACS home page), identification of markers for metastatic prostate cancer would be an important advance.

A particular problem in cancer detection and diagnosis occurs with prostate cancer. Carcinoma of the prostate (PCA) is the most frequently diagnosed cancer among men in the United States (Veltri et al., 1996). Prostate cancer was diagnosed in approximately 189,500 men in 1998 and about 40,000 men succumbed to the malignancy (Landis et al, 1998). Although relatively few prostate tumors progress to clinical significance during the lifetime of the patient, those which are progressive in nature are likely to have metastasized by the time of detection. Survival rates for individuals with metastatic prostate cancer are quite low. Between these extremes are patients with prostate tumors that will metastasize but have not yet done so, for whom surgical prostate removal is curative. Determination of which group a patient falls within is critical in determining optimal treatment and patient survival.

The FDA approval of the serum prostate specific antigen (PSA) test in 1984 changed the way that prostate disease was managed (Allhoff et al., 1989; Cooner et al., 1990; Jacobson et al, 1995; Orozco et al., 1998). PSA is widely used as a serum biomarker to detect and monitor therapeutic response in prostate cancer patients (Badalament et al., 1996; O'Dowd et al., 1997). Several modifications in PSA assays (Partin and Oesterling, 1994; Babian et al., 1996; Zlotta et al, 1997) have resulted in earlier diagnoses and improved treatment.

Although PSA has been widely used as a clinical marker of prostate cancer since 1988 (Partin and Oesterling, 1994), screening programs utilizing PSA alone or in combination with digital rectal examination (DRE) have not been successful in improving the survival rate for men with prostate cancer (Partin and Oesterling, 1994). Although PSA is specific to prostate tissue, it is produced by normal and benign as well as malignant prostatic epithelium, resulting in a high false-positive rate for prostate cancer detection (Partin and Oesterling, 1994).

While an effective indicator of prostate cancer when serum levels are relatively high, PSA serum levels are more ambiguous indicators of prostate cancer when only modestly elevated, for example when levels are between 2–10 ng/ml. At these modest elevations, serum PSA may have originated from non-cancerous disease states such as BPH (benign prostatic hyperplasia), prostatitis or physical trauma (McCormack et al, 1995). Although application of the lower 2.0 ng/ml cancer detection cutoff concentration of serum PSA has increased the diagnosis of prostate cancer, especially in younger men with nonpalpable early stage tumors (Stage Tlc) (Soh et al., 1997; Carter and Coffey, 1997; Harris et al., 1997; Orozco et al., 1998), the specificity of the PSA assay for prostate cancer detection at low serum PSA levels remains a problem.

Several investigators have sought to improve upon the specificity of serologic detection of prostate cancer by examining a variety of other biomarkers besides serum PSA concentration (Ralph and Veltri, 1997). One of the most heavily investigated of these other biomarkers is the ratio of free versus total PSA (f/t PSA) in a patient's blood. Most PSA in serum is in a molecular form that is bound to other proteins such as α1-antichymotrypsin (ACT) or α2-macroglobulin (Christensson et al, 1993; Stenman et al., 1991; Lilja et al., 1991). Free PSA is not bound to other proteins. The ratio of free to total PSA (f/tPSA) is usually significantly higher in patients with BPH compared to those with organ confined prostate cancer (Marley et al., 1996; Oesterling et al., 1995; Pettersson et al., 1995). When an appropriate cutoff is determined for the f/tPSA assay, the f/tPSA assay can help distinguish patients with BPH from those with prostate cancer in cases in which serum PSA levels are only modestly elevated (Marley et al., 1996; Partin and Oesterling, 1996). Unfortunately, while f/tPSA may improve on the detection of prostate cancer, information in the f/tPSA ratio is insufficient to improve the sensitivity and specificity of serologic detection of prostate cancer to desirable levels.

Other markers that have been used for prostate cancer detection include prostatic acid phosphatase (PAP) and prostate secreted protein (PSP). PAP is secreted by prostate cells under hormonal control (Brawn et al., 1996). It has less specificity and sensitivity than does PSA. As a result, it is used much less now, although PAP may still have some applications for monitoring metastatic patients that have failed primary treatments. In general., PSP is a more sensitive biomarker than PAP, but is not as sensitive as PSA (Huang et al., 1993). Like PSA, PSP levels are frequently elevated in patients with BPH as well as those with prostate cancer.

Another serum marker associated with prostate disease is prostate specific membrane antigen (PSMA) (Horoszewicz et al., 1987; Carter and Coffey, 1996; Murphy et al., 1996). PSMA is a Type II cell membrane protein and has been identified as Folic Acid Hydrolase (FAH) (Carter and Coffey, 1996). Antibodies against PSMA react with both normal prostate tissue and prostate cancer tissue (Horoszewicz et al., 1987). Murphy et al. (1995) used ELISA to detect serum PSMA in advanced prostate cancer. As a serum test, PSMA levels are a relatively poor indicator of prostate cancer. However, PSMA may have utility in certain circumstances. PSMA is expressed in metastatic prostate tumor capillary beds (Silver et al., 1997) and is reported to be more abundant in the blood of metastatic cancer patients (Murphy et al., 1996). PSMA messenger RNA (mRNA) is down-regulated 8–10 fold in the LNCaP prostate cancer cell line after exposure to 5-α-dihydroxytestosterone(DHT) (Israeli et al., 1994).

Two relatively new potential biomarkers for prostate cancer are human kallekrein 2 (HK2) (Piironen et al., 1996) and prostate specific transglutaminase (pTGase) (Dubbink et al., 1996). HK2 is a member of the kallekrein family that is secreted by the prostate gland (Piironen et al., 1996). Prostate specific transglutaminase is a calcium-dependent enzyme expressed in prostate cells that catalyzes post-translational cross-linking of proteins (Dubbink et al., 1996). In theory, serum concentrations of HK2 or pTGase may be of utility in prostate cancer detection or diagnosis, but the usefulness of these markers is still being evaluated.

Interleukin 8 (IL-8) has also been reported as a marker for prostate cancer. (Veltri et al., 1999). Serum IL-8 concentrations were reported to be correlated with increasing stage of prostate cancer and to be capable of differentiating BPH from malignant prostate tumors. (Id.) The wide-scale applicability of this marker for prostate cancer detection and diagnosis is still under investigation.

In addition to these protein markers for prostate cancer, severel genetic changes have been reported to be associated with prostate cancer, including: allelic loss (Bova, et al., 1993; Macoska et al., 1994; Carter et al., 1990); DNA hypermethylation (Isaacs et al., 1994); point mutations or deletions of the retinoblastoma (Rb), p53 and KAI1 genes (Bookstein et al., 1990a; Bookstein et al., 1990b; Isaacs et al., 1991; Dong et al., 1995); and aneuploidy and aneusomy of chromosomes detected by fluorescence in situ hybridization (FISH) (Macoska et al., 1994; Visakorpi et al., 1994; Takahashi et al., 1994; Alcaraz et al., 1994). None of these has been reported to exhibit sufficient sensitivity and specificity to be useful as general screening tools for asymptomatic prostate cancer.

A recent discovery was that differential expression of both full-length and truncated forms of HER2/neu oncogene receptor was correlated with prostate cancer. (An et al., 1998). Analysis by RT-PCR™ indicated that overexpression of the HER2/neu gene is associated with prostate cancer progression. (Id.)

In current clinical practice, the serum PSA assay and digital rectal exam (DRE) is used to indicate which patients should have a prostate biopsy (Lithrup et al., 1994; Orozco et al., 1998). Histological examination of the biopsied tissue is used to make the diagnosis of prostate cancer. Based upon the 189,500 cases of diagnosed prostate cancer in 1998 (Landis, 1998) and a known cancer detection rate of about 35% (Parker et al., 1996), it is estimated that in 1998 over one-half million prostate biopsies were performed in the United States (Orozco et al., 1998; Veltri et al., 1998). Clearly, there would be much benefit derived from a serological test that was sensitive enough to detect small and early stage prostate tumors that also had sufficient specificity to exclude a greater portion of patients with noncancerous or clinically insignificant conditions.

There remain deficiencies in the prior art with respect to the identification of the genes linked with the progression of prostate cancer and the development of diagnostic methods to monitor disease progression. Likewise, the identification of genes which are differentially expressed in prostate cancer would be of considerable importance in the development of a rapid, inexpensive method to diagnose cancer. Although a few prostate specific genes have been cloned (PSA, PSMA, HK2, pTGase, etc.), these are typically not up-regulated in prostate cancer. The identification of a novel, prostate specific gene that is differentially expressed in prostate cancer, compared to non-malignant prostate tissue, would represent a major, unexpected advance for the diagnosis, prognosis and treatment of prostate cancer.

SUMMARY OF THE INVENTION

The present invention addresses deficiencies in the prior art by identifying a novel, prostate specific gene that is differentially expressed in human prostate cancer compared to normal human prostate or benign prostatic hyperplasia (BPH). The encoded mRNA species and the corresponding encoded protein species have utility, for example, as markers of prostate cancer. Antibodies against the encoded protein species, as well as antisense constructs specific for the mRNA species, have utility for methods of therapeutic treatment of prostate cancer. In addition, the cDNA sequence can be used to design probes and primers for identification of a full length genomic sequence, as well as the promoter sequence for the gene, of use in the design of prostate specific expression vectors of utility in the gene therapy of prostate cancer.

The nucleic acid sequence of this novel, prostate specific gene can be used to design specific oligonucleotide probes and primers. When used in combination with nucleic acid hybridization and amplification procedures, these probes and primers permit the rapid analysis of prostate biopsy core specimens, serum samples, etc. This will assist physicians in diagnosing prostate cancer and in determining optimal treatment courses for individuals with prostate tumors of varying malignancy. The same probes and primers also may be used for in situ hybridizationor in situ PCR™ detection and diagnosis of prostate cancer.

The novel gene sequence also may be used to identify and isolate a full length genomic DNA sequence and its associated regulatory elements, including the promoter, from genomic human DNA libraries. The cDNA sequence identified in the present invention is first used to construct hybridization probes to screen genomic human DNA libraries by standard techniques. Once partial genomic clones have been identified, full-length genes are isolated by "chromosomal walking" (also called "overlap hybridization").

See, Chinault and Carbon, 1979. Nonrepetitive sequences at or near the ends of the partial genomic clones are then used as hybridization probes in further genomic library screening, ultimately allowing the isolation of entire genomic sequence for the novel prostate specific gene reported herein. Those experienced in the art will realize that full length genes may be obtained using the cDNA sequence described herein using technology currently available (Sambrook et al., 1989; Chinault and Carbon, 1979).

In the practice of this method, the cDNA sequence identified in the present disclosure is used as a hybridization probe to screen human genomic DNA libraries by standard techniques. In a preferred practice, a high quality human genomic DNA library is obtained from commercial or other sources. The library is plated on, for example, agarose plates containing nutrients, antibiotics and other standard ingredients. Individual colonies are transferred to nylon or nitrocellulose membranes and the cDNA probes are hybridized to complementary sequences on the membranes. Hybridization is detected by radioactive or enzyme-linked tags associated with the hybridized probes. Positive colonies are grown up and sequenced by, for example, dideoxy nucleotide sequencing or similar methods well known in the art. Comparison of cloned sequences with known human or animal cDNA or genomic sequences is performed using computer programs and databases well known to the skilled practitioner.

In one embodiment of the present invention, the isolated nucleic acids of the present invention are incorporated into expression vectors and expressed as the encoded proteins or peptides. Such proteins or peptides may in certain embodiments be used as antigens for induction of monoclonal or polyclonal antibody production.

One aspect of the present invention is thus, oligonucleotide hybridization probes and primers that hybridize selectively to samples of prostate cancer. These probes and primers are selected from those sequences designated herein as SEQ ID NO:1, SEQ ID NO:3 and SEQ ID NO:4. The availability of probes and primers specific for such prostate specific nucleic acid sequences, that are differentially expressed in prostate cancer, provides the basis for diagnostic kits useful for distinguishing between BPH, prostate organ confined cancer and metastatic prostate tumors. Alternatively, the availability of probes and primers that hybridize to one or more nucleic acids corresponding to SEQ ID NO:1, SEQ ID NO:3 or SEQ ID NO:4 provide the basis for diagnostic kits useful in the detection of prostate cancer.

In one broad aspect, the present invention encompasses kits for use in detecting prostate cancer cells in a biological sample. Such a kit may comprise one or more pairs of primers for amplifying nucleic acids corresponding to SEQ ID NO:1, SEQ ID NO:3 or SEQ ID NO:4. The kit may further comprise samples of total mRNA derived from tissue of various physiological states, such as normal., BPH, confined tumor and metastatically progressive tumor, for example, to be used as controls. The kit also may comprise buffers, nucleotide bases, and other compositions to be used in hybridization and/or amplification reactions. Each solution or composition may be contained in a vial or bottle and all vials held in close confinement in a box for commercial sale. Another embodiment of the present invention encompasses a kit for use in detecting prostate cancer cells in a biological sample comprising oligonucleotide probes effective to bind with high affinity to nucleic acids corresponding to SEQ ID NO:1, SEQ ID NO:3 or SEQ ID NO:4 in a Northern blot assay and containers for each of these probes. In a further embodiment, the invention encompasses a kit for use in detecting prostate cancer cells in a biological sample comprising antibodies specific for proteins encoded by nucleic acids corresponding to SEQ ID NO:1, SEQ ID NO:3 or SEQ ID NO:4, identified in the present invention.

In one broad aspect, the present invention encompasses methods for treating prostate cancer patients by administration of effective amounts of antibodies specific for the peptide products of nucleic acids corresponding to SEQ ID NO:1, SEQ ID NO:3 or SEQ ID NO:4, or by administration of effective amounts of vectors producing antisense messenger RNAs that bind to nucleic acids corresponding to SEQ ID NO:1, SEQ ID NO:3 or SEQ ID NO:4, thereby inhibiting expression of the protein products of a prostate specific gene that is overexpressed in prostate cancer. Antisense nucleic acid molecules also may be provided as RNAs, as some stable forms of RNA with a long half-life that may be administered directly without the use of a vector are now known in the art. In addition, DNA constructs may be delivered to cells by liposomes, receptor mediated transfection and other methods known in the art. Delivery of the present agents, by any means known in the art would be encompassed by the present claims.

One aspect of the present invention is novel isolated nucleic acid segments that are useful as described herein as hybridization probes and primers that specifically hybridize to nucleic acids corresponding to SEQ ID NO:1, SEQ ID NO:3 or SEQ ID NO:4. These nucleic acids are described herein as species shown to be differentially expressed in prostate cancer as compared to BPH and normal prostate tissue. The invention further comprises an isolated nucleic acid of between about 14 and about 100 bases in length, either identical to or complementary to a portion of the same length occurring within the disclosed sequences.

The present invention comprises proteins and peptides with amino acid sequences encoded by the aforementioned isolated nucleic acid segments.

The invention further comprises methods for detecting prostate cancer cells in biological samples, using hybridization primers and probes designed to specifically hybridize to nucleic acids corresponding to SEQ ID NO:1, SEQ ID NO:3 or SEQ ID NO:4. This method further comprises measuring the amounts of nucleic acid amplification products formed when primers selected from the designated sequences are used.

The invention further comprises the prognosis and/or diagnosis of prostate cancer by measuring the amounts of nucleic acid amplification products formed as above. The invention comprises methods of treating individuals with prostate cancer by providing effective amounts of antibodies and/or antisense DNA molecules which bind to the products of the above mentioned isolated nucleic acids. The invention further comprises kits for performing the above-mentioned procedures, containing antibodies, amplification primers and/or hybridization probes.

The present invention further comprises production of antibodies specific for proteins or peptides encoded by nucleic acids corresponding to SEQ ID NO:1, SEQ ID NO:3 or SEQ ID NO:4, and the use of those antibodies for diagnostic applications in detecting prostate cancer. The invention further comprises therapeutic treatment of prostate cancer by administration of effective doses of inhibitors specific for the aforementioned encoded proteins.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIG. 7. (Scanned image) Confirmation of prostate specific expression in UC41 by slot blot analysis. A human RNA master filter (Clontech, 89–514 ng of poly A⁺ RNA per lane) was probed with a UC41 specific probe as described below in the section MATERIAL AND METHODS. Expression of UC41 was examined in RNA samples from (top row) whole brain, amygdala, caudate nucleus, cerebellum, cerebral cortex, frontal lobe, hippocampus, medulla oblongata, (second row) occipital lobe, putamen, substantia nigra, temporal lobe, thalamus, nucleus acumens, spinal cord, (third row) heart, aorta, skeletal muscle, colon, bladder, uterus, prostate, dtomach, (fourth row) testis, ovary, pancreas, pituitary gland, adrenal gland, thyroid gland, salivary gland, mammary gland, (fifth row) kidney, liver, small intestine, spleen, thymus, peripheral leukocyte, lymph node, bone marrow, (sixth row) appendix, lung, trachea, placenta, (seventh row) fetal brain, fetal heart, fetal kidney, fetal liver, fetal spleen, fetal thymus, fetal lung, (bottom row) yeast total RNA, yeast tRNA, E. coli rRNA. E. coli DNA, Poly r(A), human Cotl DNA, human DNA (100ng) and human DNA (500ng).

FIGS. 8A, 8B, and 8C. Results of UC41 FISH mapping. Panel A shows the FISH signals on a metaphase chromosome. Panel B shows the same mitotic figure stained with DAPI to identify chromosome 3. Panel C shows a diagram of the FISH mapping results, wherein each dot represents the double FISH signals detected on human chromosome 3.

FIG. 9. Sequence analysis of UC41 cDNA. The UC41 cDNA sequence and predicted amino acid sequence are shown. The predicted leader sequence is indicated by the underlined box. The predicted transmembrane region is underlined in bold. The prediction of transmembrane region is based on statistical analysis of Tmbase, a database of naturally occurring transmembrane proteins.

DETAILED DESCRIPTION OF THE INVENTION

Figure 1A:
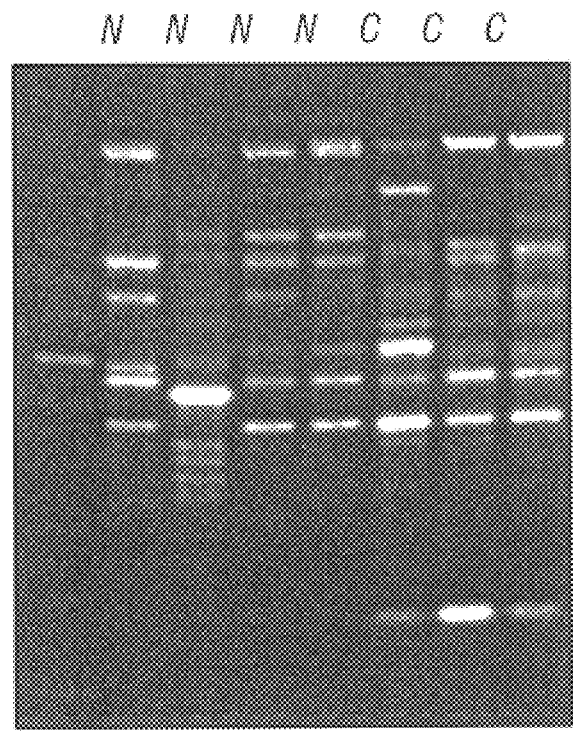
FIGS. 1A and 1B. (Scanned images) Identification of the UC41 cDNA clone and confirmation of differential expression. Panel A. Results of an agarose gel-based differential display study, comparing RNA from normal prostate tissues (N) with RNA from prostate cancer tissues (C). The position of the UC41 band is at the bottom of the panel, just above the label "UC41". Panel B. Confirmation of differential expression of UC41 by RT-PCR™ of normal prostate tissues (N) and prostate cancer tissues (C). The position of the UC41 band in this panel is adjacent to the label "UC41".

Previous work by the present inventors and others resulted in the identification of an expressed sequence tag (EST), referred to as UC41, whose expression was increased in prostate cancer cells compared to normal or benign prostate tissues. These and other results were reported in U.S. patent application Ser. No. 08/692,787, the entire text of which is incorporated herein by reference.

The present invention discloses the entire cDNA sequence of the UC41 gene (SEQ ID NO:1), and identifies UC41 as a novel, prostate specific gene whose expression is upregulated in prostate cancer. As such, the UC41 gene is an indicator of malignant transformation of prostate tissues. The skilled artisan will recognize that such a differentially expressed, prostate specific gene has utility in the early detection, diagnosis, prognosis and treatment of prostate cancer, within the scope of the present invention.

Those skilled in the art will realize that the nucleic acid sequences disclosed herein will find utility in a variety of applications in prostate cancer detection, diagnosis, prognosis and treatment. Examples of such applications within the scope of the present invention comprise amplification of one or more nucleic acids corresponding to SEQ ID NO:1, SEQ ID NO:3 or SEQ ID NO:4 using specific primers; detection of nucleic acids corresponding to SEQ ID NO: 1, SEQ ID NO:3 or SEQ ID NO:4 by hybridization with oligonucleotide probes; incorporation of isolated nucleic acids into vectors; expression of RNA, peptides or polypeptides from the vectors; development of immunologic reagents corresponding to proteins encoded by isolated nucleic acids corresponding to SEQ ID NO:1, SEQ ID NO:3 or SEQ ID NO:4; and therapeutic treatments of prostate cancer using antibodies, antisense nucleic acids, or other inhibitors specific for the identified prostate specific gene products.

4.1 Nucleic Acids

As described herein, an aspect of the present disclosure is nucleic acids corresponding to SEQ ID NO:1, SEQ ID NO:3 or SEQ ID NO:4. These sequences, in turn, correspond to: the entire cDNA sequence of UC41 (SEQ ID NO:1, FIG. 9); the cDNA sequence of UC41 that is 5' to the UC41 EST sequence disclosed in U.S. patent application Ser. No. 08/692,787 (SEQ ID NO:3, FIG. 9, bases 1–1322 of cDNA sequence); and the cDNA sequence of UC41 that is 3' to the UC41 EST sequence (SEQ ID NO:4, FIG. 9, bases 1501–1934 of cDNA sequence).

In one embodiment, the nucleic acid sequences disclosed herein will find utility as hybridization probes or amplification primers. These nucleic acids may be used, for example, in diagnostic evaluation of tissue samples or employed to clone full length genomic clones, including promoter and other regulatory sequences, corresponding thereto. In certain embodiments, these probes and primers consist of oligonucleotide fragments. Such fragments should be of sufficient length to provide specific hybridization to an RNA or DNA tissue sample. The sequences typically will be 10–20 nucleotides, but may be longer. Longer sequences, e.g., 40, 50, 100, 500 and even up to full length, are preferred for certain embodiments.

Nucleic acid molecules having contiguous stretches of about 10, 13, 15, 17, 18, 19, 20, 21, 22, 23, 24, 25, 30, 40, 50, 60, 75, 100, 200, 300, 400, 500, 600, 700, 800, 900, 1000, 1100, 1200, 1300, 1400, 1500, 1600, 1700, 1800 or 1900 nucleotides,up to the full length of the disclosed sequences, from a sequence selected from SEQ ID NO:3 and SEQ ID NO:4 are contemplated. Molecules that are complementary to the above mentioned sequences and that bind to these sequences under high stringency conditions also are contemplated. These probes will be useful in a variety of hybridization embodiments, such as Southern and Northern blotting. In some cases, it is contemplated that probes may be used that hybridize to multiple target sequences without compromising their ability to effectively diagnose cancer.

Various probes and primers can be designed around the disclosed nucleotide sequences. Primers may be of any length but, typically, are 10–20 bases in length. By assigning numeric values to a sequence, for example, the first residue is 1, the second residue is 2, etc., an algorithm defining all primers can be proposed: n to n+y where n is an integer from 1 to the last number of the sequence and y is the length of the primer minus one (9 to 19), where n+ y does not exceed the last number of the sequence. Thus, for a 10-mer, the probes correspond to bases 1 to 10, 2 to 11, 3 to 12 . . . and so on. For a 15-mer, the probes correspond to bases 1 to 15, 2 to 16, 3 to 17. . . and so on. For a 20-mer, the probes correspond to bases 1 to 20, 2 to 21, 3 to 22 . . . and so on.

The values of n in the algorithm above for each of the nucleic acid sequences is: SEQ ID NO:3, n=1322; SEQ ID NO:4, n=434.

The use of a hybridization probe of between 14 and 100 nucleotides in length allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained. One will generally prefer to design nucleic acid molecules having stretches of 20 to 30 nucleotides, or even longer where desired. Such fragments may be readily prepared by, for example, directly synthesizing the fragment by chemical means or by introducing selected sequences into recombinant vectors for recombinant production.

Accordingly, the nucleotide sequences of the invention may be used for their ability to selectively form duplex molecules with complementary stretches of genes or RNAs or to provide primers for amplification of DNA or RNA from tissues. Depending on the application envisioned, one will desire to employ varying conditions of hybridization to achieve varying degrees of selectivity of probe towards target sequence.

For applications requiring high selectivity, one will typically desire to employ relatively stringent conditions to form the hybrids, e.g., one will select relatively low salt and/or high temperature conditions, such as provided by about 0.02 M to about 0.10 M NaCl at temperatures of about 50° C. to about 70° C. Such high stringency conditions tolerate little, if any, mismatch between the probe and the template or target strand, and would be particularly suitable for isolating specific genes or detecting specific mRNA transcripts. It is generally appreciated that conditions can be rendered more stringent by the addition of increasing amounts of formamide.

For certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

The following codon chart may be used, in a site-directed mutagenic scheme, to produce nucleic acids encoding the same or slightly different amino acid sequences of a given nucleic acid:

TABLE 1

| Amino Acids | | | Codons | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

In other embodiments, hybridization may be achieved under conditions of, for example, 50 mM Tris-HCl (pH 8.3), 75 mM KCl, 3 mM MgCl$_2$, 10 mM dithiothreitol, at temperatures between approximately 20° C. to about 37° C. Other hybridization conditions utilized could include approximately 10 mM Tris-HCl (pH 8.3), 50 mM KCl, 1.5 µM MgCl$_2$, at temperatures ranging from approximately 40° C. to about 72° C.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known which can be employed to provide a detection means visible to the human eye or spectrophotometrically, to identify specific hybridization with complementary nucleic acid-containing samples.

In general., it is envisioned that the hybridization probes described herein will be useful both as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The selected conditions will depend on the particular circumstances based on the particular criteria required (depending, for example, on the G+C content, type of target nucleic acid, source of nucleic acid, size of hybridizationprobe, etc.). Following washing of the hybridized surface to remove non-specifically bound probe molecules, hybridization is detected, or even quantified, by means of the label.

It will be understood that this invention is not limited to the particular probes disclosed herein and particularly is intended to encompass at least nucleic acid sequences that are hybridizable to the disclosed sequences or are functional sequence analogs of these sequences. For example, a partial sequence may be used to identify a structurally-related gene or the full length genomic or cDNA clone from which it is derived. Those of skill in the art are well aware of the methods for generating cDNA and genomic libraries which can be used as a target for the above-described probes (Sambrook et al., 1989).

For applications in which the nucleic acid segments of the present invention are incorporated into vectors, such as plasmids, cosmids or viruses, these segments may be combined with other DNA sequences, such as promoters, polyadenylation signals, restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol.

DNA segments encoding a specific gene may be introduced into recombinant host cells and employed for expressing a specific structural or regulatory protein. Alternatively, through the application of genetic engineering techniques, subportions or derivatives of selected genes may be employed. Upstream regions containing regulatory regions such as promoter regions may be isolated and subsequently employed for expression of the selected gene.

Where an expression product is to be generated, it is possible for the nucleic acid sequence to be varied while retaining the ability to encode the same product. Reference to the codon chart, provided above, will permit those of skill in the art to design any nucleic acid encoding for the product of a given nucleic acid.

Encoded Proteins

Once the entire coding sequence of the differentially expressed, prostate specific gene has been determined, the gene can be inserted into an appropriate expression system. The gene can be expressed in any number of different recombinant DNA expression systems to generate large amounts of the polypeptide product, which can then be purified and used to vaccinate animals to generate antisera with which further studies may be conducted.

Examples of expression systems known to the skilled practitioner in the art include bacteria such as *E. coli*, yeast such as *Pichia pastoris*, baculovirus, and mammalian expression systems such as in COS or CHO cells. A complete gene can be expressed or, alternatively, fragments of the gene encoding portions of polypeptide can be produced.

In certain broad applications of the invention, the gene sequence encoding the polypeptide is analyzed to detect putative transmembrane sequences. Such sequences are typically very hydrophobic and are readily detected by the use of standard sequence analysis software, such as MacVector (IBI, New Haven, Conn.). The presence of transmembrane sequences is often deleterious when a recombinant protein is synthesized in many expression systems, especially *E. coli*, as it leads to the production of insoluble aggregates which are difficult to renature into the native conformation of the protein. Deletion of transmembrane sequences typically does not significantly alter the conformation of the remaining protein structure.

Moreover, transmembrane sequences, being by definition embedded within a membrane, are inaccessible. Antibodies to these sequences may not, therefore, prove useful in in vivo or in situ studies. Deletion of transmembrane-encoding sequences from the genes used for expression can be achieved by standard techniques. For example, fortuitously-placed restriction enzyme sites can be used to excise the desired gene fragment, or PCR™ type amplification can be used to amplify only the desired part of the gene.

Computer sequence analysis may be used to determine the location of the predicted major antigenic determinant epitopes of the polypeptide. Software capable of carrying out this analysis is readily available commercially, for example MacVector (IBI, New Haven, Conn.). The software typically uses standard algorithms such as the Kyte/Doolittle or Hopp/Woods methods for locating hydrophilic sequences may be found on the surface of proteins and are, therefore, likely to act as antigenic determinants.

Once this analysis is made, polypeptides may be prepared which contain at least the essential features of the antigenic determinant and which may be employed in the generation of antisera against the polypeptide. Minigenes or gene fusions encoding these determinants may be constructed and inserted into expression vectors by standard methods, for example, using PCR™ cloning methodology.

The gene or gene fragment encoding a polypeptide may be inserted into an expression vector by standard subcloning techniques. An *E. coli* expression vector may be used which produces the recombinant polypeptide as a fusion protein, allowing rapid affinity purification of the protein. Examples of such fusion protein expression systems are the glutathione S-transferase system (Pharmacia, Piscataway, N.J.), the maltose binding protein system (NEB, Beverley, Mass.), the FLAG system (IBI, New Haven, Conn.), and the 6×His system (Qiagen, Chatsworth, Calif.).

Some of these systems produce recombinant polypeptides bearing only a small number of additional amino acids, which are unlikely to affect the antigenic ability of the recombinant polypeptide. For example, both the FLAG system and the 6×His system add only short sequences, both of which are known to be poorly antigenic and which do not adversely affect folding of the polypeptide to its native conformation. Other fusion systems are designed to produce fusions wherein the fusion partner is easily excised from the desired polypeptide. In one embodiment, the fusion partner is linked to the recombinant polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

The expression system used also may be one driven by the baculovirus polyhedron promoter. The gene encoding the polypeptide may be manipulated by standard techniques in order to facilitate cloning into the baculovirus vector. One baculovirus vector is the pBlueBac vector (Invitrogen, Sorrento, Calif.). The vector carrying the gene for the polypeptide is transfected into *Spodoptera frugiperda* (Sf9) cells by standard protocols, and the cells are cultured and processed to produce the recombinant antigen. See Summers et al., U.S. Pat. No. 4,215,051 (incorporated herein by reference).

As an alternative to recombinant polypeptides, synthetic peptides corresponding to the antigenic determinants may be prepared. Such peptides are at least six amino acid residues long, and may contain up to approximately 35 residues, which is the approximate upper length limit of automated peptide synthesis machines, such as those available from Applied Biosystems (Foster City, Calif.). Use of such small peptides for vaccination typically requires conjugation of the peptide to an immunogenic carrier protein such as hepatitis B surface antigen, keyhole limpet hemocyanin or bovine serum albumin. Methods for performing this conjugation are well known in the art.

Amino acid sequence variants of the polypeptide also may be prepared. These may, for instance, be minor sequence variants of the polypeptide which arise due to natural variation within the population or they may be homologues found in other species. They also may be sequences which do not occur naturally but which are sufficiently similar that they function similarly and/or elicit an immune response that cross-reacts with natural forms of the polypeptide. Sequence variants may be prepared by standard methods of sitedirected mutagenesis such as those described herein for removing the transmembrane sequence.

Amino acid sequence variants of the polypeptide may be substitutional., insertional or deletion variants. Deletion variants lack one or more residues of the native protein which are not essential for function or immunogenic activity, and are exemplified by the variants lacking a transmembrane sequence. Another common type of deletion variant is one lacking secretory signal sequences or signal sequences directing a protein to bind to a particular part of a cell. An example of the latter sequence is the SH2 domain, which induces protein binding to phosphotyrosine residues.

Substitutional variants typically contain an alternative amino acid at one or more sites within the protein, and may be designed to modulate one or more properties of the polypeptide such as stability against proteolytic cleavage. Substitutions preferably are conservative, that is, one amino acid is replaced with one of similar size and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

Insertional variants include fusion proteins such as those used to allow rapid purification of the polypeptide and also may include hybrid proteins containing sequences from other proteins and polypeptides which are homologues of the polypeptide. For example, an insertional variant may include portions of the amino acid sequence of the polypeptide from one species, together with portions of the homologous polypeptide from another species. Other insertional variants may include those in which additional amino acids are introduced within the coding sequence of the polypeptide. These typically are smaller insertions than the fusion proteins described above and are introduced, for example, to disrupt a protease cleavage site.

Major antigenic determinants of the polypeptide may be identified by an empirical approach in which portions of the gene encoding the polypeptide are expressed in a recombinant host, and the resulting proteins tested for their ability to elicit an immune response. For example, PCR™ may be used to prepare a range of peptides lacking successively longer fragments of the C-terminus of the protein. The immunoprotective activity of each of these peptides then identifies those fragments or domains of the polypeptide which are essential for this activity. Further studies in which only a small number of amino acids are removed at each iteration then allows the location of the antigenic determinants of the polypeptide.

Another method for the preparation of the polypeptides according to the invention is the use of peptide mimetics. Mimetics are peptide-containing molecules which mimic elements of protein secondary structure. See, for example, Johnson et al. (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule.

Successful applications of the peptide mimetic concept have thus far focused on mimetics of β-turns within proteins, which are known to be highly antigenic. Likely β-turn structure within a polypeptide may be predicted by computer-based algorithms as discussed herein. Once the component amino acids of the turn are determined, peptide mimetics may be constructed to achieve a similar spatial orientation of the essential elements of the amino acid side chains.

4.3 Preparation of Antibodies Specific for Encoded Proteins 4.3.1 Expression of Proteins from Cloned cDNAs The cDNA species specified in SEQ ID NO:1, SEQ ID NO:3 and SEQ ID NO:4.may be expressed as encoded peptides or proteins. The engineering of DNA segment(s) for expression in a prokaryotic or eukaryotic system may be performed by techniques generally known to those of skill in recombinant expression. It is believed that virtually any expression system may be employed in the expression of the claimed nucleic acid sequences.

Both cDNA and genomic sequences are suitable for eukaryotic expression, as the host cell will generally process the genomic transcripts to yield functional mRNA for translation into protein. In addition, it is possible to use partial sequences for generation of antibodies against discrete portions of a gene product, even when the entire sequence of that gene product remains unknown. Computer programs are available to aid in the selection of regions which have potential immunologic significance. For example, software capable of carrying out this analysis is readily available commercially from MacVector (IBI, New Haven, Conn.). The software typically uses standard algorithms such as the Kyte/Doolittle or Hopp/Woods methods for locating hydrophilic sequences which are characteristically found on the surface of proteins and are, therefore, likely to act as antigenic determinants.

As used herein, the terms "engineered" and "recombinant" cells are intended to refer to a cell into which an exogenous DNA segment or gene, such as a cDNA or gene has been introduced through the hand of man. Therefore, engineered cells are distinguishable from naturally occurring cells which do not contain a recombinantly introduced exogenous DNA segment or gene. Recombinant cells include those having an introduced cDNA or genomic gene, and also include genes positioned adjacent to a heterologous promoter not naturally associated with the particular introduced gene.

To express a recombinant encoded protein or peptide, whether mutant or wild-type, in accordance with the present invention one would prepare an expression vector that comprises one of the claimed isolated nucleic acids under the control of, or operatively linked to, one or more promoters. To bring a coding sequence "under the control of" a promoter, one positions the 5' end of the transcription initiation site of the transcriptional reading frame generally between about 1 and about 50 nucleotides "downstream" (i.e., 3') of the chosen promoter. The "upstream" promoter stimulates transcription of the DNA and promotes expression of the encoded recombinant protein. This is the meaning of "recombinant expression" in this context.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E coli* and *B. subtilis* transformed with recombinant bacteriophage DNA, plasmid DNA or cosmid DNA expression vectors.

Certain examples of prokaryotic hosts are *E. coli* strain RR1, *E. coli* LE392, *E. coli* B, *E. coli* X 1776 (ATCC No. 31537) as well as *E. coli* W3110 (F-, lambda-, prototrophic, ATCC No. 273325); bacilli such as *Bacillus subtilis*; and other enterobacteriaceae such as *Salmonella typhimurium, Serratia marcescens*, and various Pseudomonas species.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is often transformed using pBR322, a plasmid derived from an *E. coli* species. pBR322 contains genes for ampicillin and tetracycline resistance and thus provides a simple means for identifying transformed cells. The pBR plasmid, or other microbial plasmid or phage must also contain, or be modified to contain, promoters which may be used by the microbial organism for expression of its own proteins.

In addition, phage vectors containing replicon and control sequences that are compatible with the host microorganism may be used as transforming vectors in connection with these hosts. For example, the phage lambda GEM™-11 may be utilized in making a recombinant phage vector which may be used to transform host cells, such as *E. coli* LE392.

Further useful vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, or the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in Saccharomyces, the plasmid YRp7, for example, is commonly used (Stinchcomb et al., 1979; Kingsman et al., 1979; Tschemper et al., 1980). This plasmid already contains the trpl gene which provides a selection marker for a mutant strain of yeast lacking the ability to grow in tryptophan, for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al, 1968; Holland et al., 1978), such as enolase, glyceraldehyde-3-phosphatedehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms also may be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more coding sequences.

In a useful insect system, *Autographa californica* nuclear polyhidrosis virus (AcNPV) is used as a vector to express foreign genes. The virus grows in *Spodoptera frugiperda* cells. The isolated nucleic acid coding sequences are cloned into non-essential regions (for example the polyhedrin gene) of the virus and placed under control of an AcNPV promoter (for example the polyhedrin promoter). Successful insertion of the coding sequences results in the inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., U.S. Pat. No. 4,215,051 (Smith)).

Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the encoded protein.

Different host cells have characteristic and specific mechanisms for the post-translational processing and modification of proteins. Appropriate cells lines or host systems may be chosen to ensure the correct modification and processing of the foreign protein expressed. Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments also may be used, provided there is included the approximately 250 bp sequence extending from the HindIII site toward the Bgl I site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals also may be required for efficient translation of the claimed isolated nucleic acid coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons may be of a variety of origins, both natural and synthetic. The efficiency of expression may be enhanced by the inclusion of appropriate transcription enhancer elements or transcription terminators (Bittner et al., 1987).

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells may be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn may be cloned and expanded into cell lines.

A number of selection systems may be used, including but not limited to, the herpes simplex virus thymidine kinase (Wigler et al., 1977), hypoxanthine-guanine phosphoribosyltransferase (Szybalska et al., 1962) and adenine phosphoribosyltransferase genes (Lowy et al., 1980), in tk-, hgprt- or aprt-cells, respectively. Also, antimetabolite resistance may be used as the basis of selection for dhfr, that confers resistance to methotrexate (Wigler et al., 1980; O'Hare et al., 1981); gpt, that confers resistance to mycophenolic acid (Mulligan et al., 1981;); neo, that confers resistance to the aminoglycoside G-418 (Colberre-Garapinet al., 1981); and hygro, that confers resistance to hygromycin (Santerre et al., 1984).

It is contemplated that the isolated nucleic acids of the invention may be "overexpressed," i.e., expressed in increased levels relative to its natural expression in human prostate, cells, or even relative to the expression of other proteins in the recombinant host cell. Such overexpression may be assessed by a variety of methods, including radiolabeling and/or protein purification. However, simple and direct methods are preferred, for example, those involving SDS/PAGE and protein staining or Western blotting, followed by quantitative analyses, such as densitometric scanning of the resultant gel or blot. A specific increase in the level of the recombinant protein or peptide in comparison to the level in natural human prostate, cells is indicative of overexpression, as is a relative abundance of the specific protein in relation to the other proteins produced by the host cell and, e.g., visible on a gel.

4.3.2 Purification of Expressed Proteins

Further aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state, i.e., in this case, relative to its purity within a prostate, cell extract. A purified protein or peptide therefore also refers to a protein or peptide, free from the environment in which it may naturally occur.

Generally, "purified" will refer to a protein or peptide composition which has been subjected to fractionation to remove various other components, and which composition substantially retains its expressed biological activity. Where the term "substantially purified" is used, this will refer to a composition in which the protein or peptide forms the major component of the composition, such as constituting about 50% or more of the proteins in the composition.

Various methods for quantifying the degree of purification of the protein or peptide will be known to those of skill in the art in light of the present disclosure. These include, for example, determining the specific activity of an active fraction, or assessing the number of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in the most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater-fold purification than the same technique utilizing a low pressure chromatography system. Methods exhibiting a lower degree of relative purification may have advantages in total recovery of protein product, or in maintaining the activity of an expressed protein.

It is known that the migration of a polypeptide may vary, sometimes significantly, with different conditions of SDS/PAGE (Capaldi et al., 1977). It will therefore be appreciated that under differing electrophoresis conditions, the apparent molecular weights of purified or partially purified expression products may vary.

4.3.3 Antibody Generation

For some embodiments, it will be desirable to produce antibodies that bind with high specificity to the polypeptide product(s) of an isolated nucleic acid selected from SEQ ID NO: I, SEQ ID NO:3 and SEQ ID NO:4. Means for preparing and characterizing antibodies are well known in the art (See, e.g., Antibodies: A Laboratory Manual., Cold Spring Harbor Laboratory, 1988; incorporated herein by reference).

Methods for generating polyclonal antibodies are well known in the art. Briefly, a polyclonal antibody is prepared by immunizing an animal with an immunogenic composition and collecting antisera from that immunized animal. A wide range of animal species may be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin also may be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine.

As is also well known in the art, the immunogenicity of a particular immunogen composition may be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes may be used to administer the immunogen (subcutaneous, intramuscular, intradermal., intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal may be bled and the serum isolated and stored, and/or the animal may be used to generate MAbs. For production of rabbit polyclonal antibodies, the animal may be bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody or a peptide bound to a solid matrix.

Monoclonal antibodies (MAbs) may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified expressed protein, polypeptide or peptide. The immunizing composition is administered in a manner effective to stimulate antibody producing cells.

The methods for generating monoclonal antibodies (MAbs) generally begin along the same lines as those for preparing polyclonal antibodies. Rodents such as mice and rats are preferred animals, however, the use of rabbit, sheep or frog cells is also possible. The use of rats may provide certain advantages (Goding, 1986, pp. 60–61), but mice are preferred, with the BALB/c mouse being most preferred as this is most routinely used and generally gives a higher percentage of stable fusions.

The animals are injected with antigen as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of the animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). For example, where the immunized animal is a mouse, one may use P3-X63/Ag8, X63-Ag8.653, NS1/1.Ag 4 1, Sp210-Ag14, FO, NSO/JU, MPC-11, MPC11-X45-GTG 1.7 and S194/5XXO Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding pp. 71–74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental., unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells may operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones may then be propagated indefinitely to provide MAbs. The cell lines may be exploited for MAb production in two basic ways. A sample of the hybridoma may be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, may then be tapped to provide MAbs in high concentration. The individual cell lines also may be cultured in vitro, where the MAbs are naturally secreted into the culture medium from which they may be readily obtained in high concentrations. MAbs produced by either means may be further purified, if desired, using filtration, centrifugation and various chromatographic methods such as HPLC or affinity chromatography.

Large amounts of the monoclonal antibodies of the present invention also may be obtained by multiplying hybridoma cells in vivo. Cell clones are injected into mammals which are histocompatible with the parent cells, e.g., syngeneic mice, to cause growth of antibody-producing tumors. Optionally, the animals are primed with a hydrocarbon, especially oils such as pristane (tetramethylpentadecane) prior to injection.

In accordance with the present invention, fragments of the monoclonal antibody of the invention may be obtained from the monoclonal antibody produced as described above, by methods which include digestion with enzymes such as pepsin or papain and/or cleavage of disulfide bonds by chemical reduction. Alternatively, monoclonal antibody fragments encompassed by the present invention may be synthesized using an automated peptide synthesizer.

The monoclonal conjugates of the present invention are prepared by methods known in the art, e.g., by reacting a monoclonal antibody prepared as described above with, for instance, an enzyme in the presence of a coupling agent such as glutaraldehyde or periodate. Conjugates with fluorescein markers are prepared in the presence of these coupling agents or by reaction with an isothiocyanate. Conjugates with metal chelates are similarly produced. Other moieties to which antibodies may be conjugated include radionuclides such as $^3$H, $^{125}$I, $^{131}$I, $^{32}$P, $^{35}$S, $^{14}$C, $^{51}$Cr, $^{36}$Cl, $^{57}$Co, $^{58}$Co, $^{59}$Fe, $^{75}$Se, $^{152}$Eu, and $^{99m}$Tc. Radioactively labeled monoclonal antibodies of the present invention are produced according to well-known methods in the art. For instance, monoclonal antibodies may be iodinated by contact with sodium or potassium iodide and a chemical oxidizing agent such as sodium hypochlorite, or an enzymatic oxidizing agent, such as lactoperoxidase. Monoclonal antibodies according to the invention may be labeled with technetium-$^{99}$ by ligand exchange process, for example, by reducing pertechnate with stannous solution, chelating the reduced technetium onto a Sephadex column and applying the antibody to this column or by direct labeling techniques, e.g., by incubating pertechnate, a reducing agent such as SNCl$_2$, a buffer solution such as sodium-potassium phthalate solution, and the antibody.

It will be appreciated by those of skill in the art that monoclonal or polyclonal antibodies specific for proteins that are preferentially expressed in metastatic or nonmetastatic human prostate cancer will have utilities in several types of applications. These may include the production of diagnostic kits for use in detecting or diagnosing human prostate cancer. An alternative use would be to link such antibodies to therapeutic agents, such as chemotherapeutic agents, followed by administration to individuals with prostate cancer, thereby selectively targeting the prostate cancer cells for destruction. The skilled practitioner will realize that such uses are within the scope of the present invention.

4.4 Immunodetection Assays 4.4.1 Immunodetection Methods

In still further embodiments, the present invention concerns immunodetection methods for binding, purifying, removing, quantifying or otherwise generally detecting biological components. The encoded proteins or peptides of the present invention may be employed to detect antibodies having reactivity therewith, or, alternatively, antibodies prepared in accordance with the present invention, may be employed to detect the encoded proteins or peptides. The steps of various useful immunodetection methods have been described in the scientific literature, such as, e.g., Nakamura et al. (1987).

In general., the immunobinding methods include obtaining a sample suspected of containing a protein, peptide or antibody, and contacting the sample with an antibody or protein or peptide in accordance with the present invention, as the case may be, under conditions effective to allow the formation of immunocomplexes.

The immunobinding methods include methods for detecting or quantifying the amount of a reactive component in a sample, which methods require the detection or quantitation of any immune complexes formed during the binding process. Here, one would obtain a sample suspected of containing a prostate specific protein, peptide or a corresponding antibody, and contact the sample with an antibody or encoded protein or peptide, as the case may be, and then detect or quantify the amount of immune complexes formed under the specific conditions.

In terms of antigen detection, the biological sample analyzed may be any sample that is suspected of containing a prostate cancer-specific antigen, such as a prostate or lymph node tissue section or specimen, a homogenized tissue extract, an isolated cell, a cell membrane preparation, separated or purified forms of any of the above protein-containing compositions, or even any biological fluid that comes into contact with prostate tissues, including blood or lymphatic fluid.

Contacting the chosen biological sample with the protein, peptide or antibody under conditions effective and for a period of time sufficient to allow the formation of immune complexes (primary immune complexes) is generally a matter of simply adding the composition to the sample and incubating the mixture for a period of time long enough for the antibodies to form immune complexes with, i. e., to bind to, any antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general., the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. Patents concerning the use of such labels include 3,817,837; 3,850,752; 3,939, 350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The encoded protein, peptide or corresponding antibody employed in the detection may itself be linked to a detectable label, wherein one would then simply detect this label, thereby allowing the amount of the primary immune complexes in the composition to be determined.

Alternatively, the first added component that becomes bound within the primary immune complexes may be detected by means of a second binding ligand that has binding affinity for the encoded protein, peptide or corresponding antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the encoded protein, peptide or corresponding antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplificationif this is desired.

The immunodetection methods of the present invention have evident utility in the diagnosis of conditions such as prostate cancer. Here, a biological or clinical sample suspected of containing either the encoded protein or peptide or corresponding antibody is used. However, these embodiments also have applications to non-clinical samples, such as in the titering of antigen or antibody samples, in the selection of hybridomas, and the like.

In the clinical diagnosis or monitoring of patients with prostate cancer, the detection of an antigen encoded by a nucleic acid corresponding to SEQ ID NO: 1, SEQ ID NO:3 or SEQ ID NO:4, or an increase in the levels of such an antigen, in comparison to the levels in a corresponding biological sample from a normal subject is indicative of a patient with prostate cancer. The basis for such diagnostic methods lies, in part, with the finding that the novel prostate specific gene identified in the present invention is overexpressed in prostate cancer tissue samples (see Examples below). By extension, it may be inferred that said gene produces elevated levels of encoded protein(s), that may be used as prostate cancer markers.

Those of skill in the art are very familiar with differentiating between significant expression of a prostate specific gene, which represents a positive identification, and low level or background expression of the same gene. Indeed, background expression levels are often used to form a "cut-off" above which increased staining will be scored as significant or positive. Significant expression may be represented by high levels of antigens in tissues or within body fluids, or alternatively, by a high proportion of cells from within a tissue that each give a positive signal.

4.4.2 Immunohistochemistry

The antibodies of the present invention may be used in conjunction with both fresh-frozen and formalin-fixed, paraffin-embedded tissue blocks prepared by immunohistochemistry(IHC). Any IHC method well known in the art may be used such as those described in *Diagnostic Immunopathology*, 2nd edition. edited by, Robert B. Colvin, Atul K. Bhan and Robert T. McCluskey. Raven Press, New York., 1995, (incorporated herein by reference) and in particular, Chapter 31 of that reference entitled Gynecological and GenitourinaryTumors (pages 579–597), by Debra A. Bell, Robert H. Young and Robert E. Scully and references therein.

4.4.3 ELISA

As noted, it is contemplated that the encoded proteins or peptides of the invention will find utility as immunogens, e.g., in connection with vaccine development, in immunohistochemistry and in ELISA assays. One evident utility of the encoded antigens and corresponding antibodies is in immunoassays for the detection of prostate cancer specific proteins, as needed in diagnosis and prognostic monitoring.

Immunoassays, in their most simple and direct sense, are binding assays. Certain preferred immunoassays are the various types of enzyme linked immunosorbent assays (ELISAs) and radioimmunoassays(RIA) known in the art. Immunohistochemicaldetection using tissue sections is also particularly useful. However, it will be readily appreciated that detection is not limited to such techniques, and Western blotting, dot blotting, FACS analyses, and the like also may be used.

In one exemplary ELISA, antibodies binding to the encoded proteins of the invention are immobilized onto a selected surface exhibiting protein affinity, such as a well in a polystyrene microtiter plate. Then, a test composition suspected of containing the prostate cancer marker antigen, such as a clinical sample, is added to the wells. After binding and washing to remove non-specifically bound immunecomplexes, the bound antigen may be detected. Detection is generally achieved by the addition of a second antibody specific for the target protein, that is linked to a detectable label. This type of ELISA is a simple "sandwich ELISA." Detection also may be achieved by the addition of a second antibody, followed by the addition of a third antibody that has binding affinity for the second antibody, with the third antibody being linked to a detectable label.

In another exemplary ELISA, the samples suspected of containing the prostate cancer marker antigen are immobilized onto the well surface and then contacted with the antibodies of the invention. After binding and washing to remove non-specifically bound immunecomplexes, the bound antigen is detected. Where the initial antibodies are linked to a detectable label, the immunecomplexes may be detected directly. Again, the immunecomplexes may be detected using a second antibody that has binding affinity for the first antibody, with the second antibody being linked to a detectable label.

Another ELISA in which the proteins or peptides are immobilized, involves the use of antibody competition in the detection. In this ELISA, labeled antibodies are added to the wells, allowed to bind to the prostate cancer marker protein, and detected by means of their label. The amount of marker antigen in an unknown sample is then determined by mixing the sample with the labeled antibodies before or during incubation with coated wells. The presence of marker antigen in the sample acts to reduce the amount of antibody available for binding to the well and thus reduces the ultimate signal. This is appropriate for detecting antibodies in an unknown sample, where the unlabeled antibodies bind to the wells and also reduces the amount of antigen available to bind the labeled antibodies.

Irrespective of the format employed, ELISAs have certain features in common, such as coating, incubating or binding, washing to remove non-specifically bound species, and detecting the bound immunecomplexes. These are described as follows:

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material., the immobilizing surface is contacted with the control human prostate, cancer and/or clinical or biological sample to be tested under conditions effective to allow immunecomplex (antigen/antibody) formation. Detection of the immunecomplex then requires a labeled secondary binding ligand or antibody, or a secondary binding ligand or antibody in conjunction with a labeled tertiary antibody or third binding ligand.

"Under conditions effective to allow immunecomplex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 h, at temperatures preferably on the order of 25° to 27° C., or may be overnight at about 4° C. or so.

Following all incubation steps in an ELISA, the contacted surface is washed so as to remove non-complexed material.

A preferred washing procedure includes washing with a solution such as PBS/Tween, or borate buffer. Following the formation of specific immunecomplexes between the test sample and the originally bound material, and subsequent washing, the occurrence of even minute amounts of immunecomplexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immunecomplex with a urease, glucose oxidase, alkaline phosphatase or hydrogen peroxidase-conjugated antibody for a period of time and under conditions that favor the development of further immunecomplex formation (e.g., incubation for 2 h at room temperature in a PBS-containing solution such as PBS-Tween).

After incubation with the labeled antibody, and subsequent to washing to remove unbound material., the amount of label is quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation is then achieved by measuring the degree of color generation, e.g., using a visible spectra spectrophotometer.

4.4.4 Use of Antibodies for Radioimaging

The antibodies of this invention will be used to quantify and localize the expression of the encoded marker proteins. The antibody, for example, will be labeled by any one of a variety of methods and used to visualize the localized concentration of the cells producing the encoded protein.

The invention also relates to an in vivo method of imaging a pathological prostate, cancer condition using the above described monoclonal antibodies. Specifically, this method involves administering to a subject an imaging-effective amount of a detectably-labeled prostate, cancer-specific monoclonal antibody or fragment thereof and a pharmaceutically effective carrier and detecting the binding of the labeled monoclonal antibody to the diseased tissue. The term "in vivo imaging" refers to any method which permits the detection of a labeled monoclonal antibody of the present invention or fragment thereof that specifically binds to a diseased tissue located in the subject's body. A "subject" is a mammal, preferably a human. An "imaging effective amount" means that the amount of the detectably-labeled monoclonal antibody, or fragment thereof, administered is sufficient to enable detection of binding of the monoclonal antibody or fragment thereof to the diseased tissue.

A factor to consider in selecting a radionuclide for in vivo diagnosis is that the half-life of a nuclide be long enough so that it is still detectable at the time of maximum uptake by the target, but short enough so that deleterious radiation upon the host, as well as background, is minimized. Ideally, a radionuclide used for in vivo imaging will lack a particulate emission, but produce a large number of photons in a 140–2000 keV range, which may be readily detected by conventional gamma cameras.

A radionuclide may be bound to an antibody either directly or indirectly by using an intermediary functional group. Intermediary functional groups which are often used to bind radioisotopes which exist as metallic ions to antibody are diethylenetriaminepentaacetic acid (DTPA) and ethylene diaminetetracetic acid (EDTA). Examples of metallic ions suitable for use in this invention are $^{99m}Tc$, $^{123}I$, $^{111}In$, $^{131}I$, $^{97}Ru$, $^{67}Cu$, $^{67}Ga$, $^{125}I$, $^{68}Ga$, $^{72}As$, $^{89}Zr$, and $^{201}Tl$.

In accordance with this invention, the monoclonal antibody or fragment thereof may be labeled by any of several techniques known to the art. The methods of the present invention also may use paramagnetic isotopes for purposes of in vivo detection. Elements particularly useful in Magnetic Resonance Imaging ("MRI") include $^{157}Gd$, $^{55}Mn$, $^{162}Dy$, $^{52}Cr$, and $^{56}Fe$.

Administration of the labeled antibody may be local or systemic and accomplished intravenously, intraarterially, via the spinal fluid or the like. Administration also may be intradermal or intracavitary, depending upon the body site under examination. After a sufficient time has lapsed for the monoclonal antibody or fragment thereof to bind with the diseased tissue, for example 30 min to 48 h, the area of the subject under investigation is examined by routine imaging techniques such as MRI, SPECT, planar scintillation imaging and emerging imaging techniques, as well. The exact protocol will necessarily vary depending upon factors specific to the patient, as noted above, and depending upon the body site under examination, method of administration and type of label used; the determination of specific procedures would be routine to the skilled artisan. The distribution of the bound radioactive isotope and its increase or decrease with time is then monitored and recorded. By comparing the results with data obtained from studies of clinically normal individuals, the presence and extent of the diseased tissue may be determined.

It will be apparent to those of skill in the art that a similar approach may be used to radio-image the production of the encoded prostate cancer marker proteins in human patients. The present invention provides methods for the in vivo diagnosis of prostate, cancer in a patient. Such methods generally comprise administering to a patient an effective amount of a prostate, cancer specific antibody, which antibody is conjugated to a marker, such as a radioactive isotope or a spin-labeled molecule, that is detectable by non-invasive methods. The antibody-marker conjugate is allowed sufficient time to come into contact with reactive antigens that be present within the tissues of the patient, and the patient is then exposed to a detection device to identify the detectable marker.

4.4.5 Kits

In still further embodiments, the present invention concerns immunodetection kits for use with the immunodetection methods described above. As the encoded proteins or peptides may be employed to detect antibodies and the corresponding antibodies may be employed to detect encoded proteins or peptides, either or both of such components may be provided in the kit. The immunodetection kits will thus comprise, in suitable container means, an encoded protein or peptide, or a first antibody that binds to an encoded protein or peptide, and an immunodetection reagent.

In certain embodiments, the encoded protein or peptide, or the first antibody that binds to the encoded protein or peptide, may be bound to a solid support, such as a column matrix or well of a microtiter plate.

The immunodetection reagents of the kit may take any one of a variety of forms, including those detectable labels that are associated with or linked to the given antibody or antigen, and detectable labels that are associated with or attached to a secondary binding ligand. Exemplary secondary ligands are those secondary antibodies that have binding affinity for the first antibody or antigen, and secondary antibodies that have binding affinity for a human antibody.

Further suitable immunodetection reagents for use in the present kits include the two-component reagent that comprises a secondary antibody that has binding affinity for the first antibody or antigen, along with a third antibody that has binding affinity for the second antibody, the third antibody being linked to a detectable label.

The kits may further comprise a suitably aliquoted composition of the encoded protein or polypeptide antigen, whether labeled or unlabeled, as may be used to prepare a standard curve for a detection assay.

The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial., test tube, flask, bottle, syringe or other container means, into which the antibody or antigen may be placed, and preferably, suitably aliquoted. Where a second or third binding ligand or additional component is provided, the kit will also generally contain a second, third or other additional container into which this ligand or component may be placed. The kits of the present invention will also typically include a means for containing the antibody, antigen, and any other reagent containers in close confinement for commercial sale. Such containers may include injection or blow-molded plastic containers into which the desired vials are retained.

4.5 Detection and Quantitation of RNA Species

One embodiment of the instant invention comprises a method for identification of prostate cancer cells in a biological sample by amplifying and detecting nucleic acids corresponding to the novel prostate specific gene (UC41) reported herein. The biological sample may be any tissue or fluid in which prostate cancer cells might be present. Various embodiments include radical prostatectomy specimens, pathological specimens, bone marrow aspirate, bone marrow biopsy, lymph node aspirate, lymph node biopsy, spleen tissue, fine needle aspirate, skin biopsy or organ tissue biopsy. Other embodiments include samples where the body fluid is peripheral blood, serum, plasma, lymph fluid, ascites, serous fluid, pleural effusion, sputum, cerebrospinal fluid, lacrimal fluid, stool, prostatic fluid or urine.

Nucleic acid used as a template for amplification is isolated from cells contained in the biological sample, according to standard methodologies. (Sambrook et al., 1989) The nucleic acid may be genomic DNA or fractionated or whole cell RNA. Where RNA is used, it may be desired to convert the RNA to a complementary cDNA. In one embodiment, the RNA is whole cell RNA and is used directly as the template for amplification.

Pairs of primers that selectively hybridize to nucleic acids corresponding to SEQ ID NO:1, SEQ ID NO:3 or SEQ ID NO:4 are contacted with the isolated nucleic acid under conditions that permit selective hybridization. Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology; Bellus, 1994).

Following detection, one may compare the results seen in a given patient with a statistically significant reference group of normal patients and prostate, cancer patients. In this way, it is possible to correlate the amount of nucleic acid detected with various clinical states.

4.5.1 Primers

The term primer, as defined herein, is meant to encompass any nucleic acid that is capable of priming the synthesis of a nascent nucleic acid in a template-dependent process.

Typically, primers are oligonucleotides from ten to twenty base pairs in length, but longer sequences may be employed. Primers may be provided in double-stranded or single-stranded form, although the single-stranded form is preferred.

4.5.2 Template Dependent Amplification Methods

A number of template dependent processes are available to amplify the nucleic acid sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in its entirety.

Briefly, in PCR™, two primer sequences are prepared which are complementary to regions on opposite complementary strands of the target nucleic acid sequence. An excess of deoxynucleoside triphosphates are added to a reaction mixture along with a DNA polymerase, e.g., Taq polymerase. If the target nucleic acid sequence is present in a sample, the primers will bind to the target nucleic acid and the polymerase will cause the primers to be extended along the target nucleic acid sequence by adding on nucleotides. By raising and lowering the temperature of the reaction mixture, the extended primers will dissociate from the target nucleic acid to form reaction products, excess primers will bind to the target nucleic acid and to the reaction products and the process is repeated.

A reverse transcriptase PCR™ amplification procedure may be performed in order to quantify the amount of mRNA amplified. Methods of reverse transcribing RNA into cDNA are well known and described in Sambrook et al., 1989. Alternative methods for reverse transcription utilize thermostable DNA polymerases. These methods are described in WO 90/07641 filed Dec. 21, 1990. Polymerase chain reaction methodologies are well known in the art.

Another method for amplification is the ligase chain reaction ("LCR"), disclosed in European Application No. 320 308, incorporated herein by reference in its entirely. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, also may be used as still another amplification method in the present invention. In this method, a replicative sequence of RNA which has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[α-thio]-triphosphates in one strand of a restriction site also may be useful in the amplification of nucleic acids in the present invention. Walker et al. (1992), incorporated herein by reference in its entirety.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases may be added as biotinylated derivatives for easy detection. A similar approach is used in SDA. Target specific sequences also may be detected using a cyclic probe reaction (CPR). In CPR, a probe having 3' and 5' sequences of non-specific DNA and a middle sequence of specific RNA is hybridized to DNA which is present in a sample. Upon hybridization, the reaction is treated with RNase H, and the products of the probe identified as distinctive products which are released after digestion. The original template is annealed to another cycling probe and the reaction is repeated.

Still other amplification methods described in GB Application No. 2 202 328, and in PCT Application No. PCT/US89/01025, each of which is incorporated herein by reference in its entirety, may be used in accordance with the present invention. In the former application, "modified" primers are used in a PCR™ like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR. Kwoh et aL (1989); Gingeras et al., PCT Application WO 88/10315, incorporated herein by reference in their entirety. In NASBA, the nucleic acids may be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once against with a polymerase such as T7 or SP6. The resulting products, whether truncated or complete, indicate target specific sequences.

Davey et al., European Application No. 329 822 (incorporated herein by reference in its entirely) disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a second template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence may be used by the appropriate RNA polymerase to make many RNA copies of the DNA. These copies may then re-enter the cycle leading to very swift amplification. With proper choice of enzymes, this amplification may be done isothermally without addition of enzymes at each cycle. Because of the cyclical nature of this process, the starting sequence may be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR™." Frohman (1990) and Ohara et al. (1989), each herein incorporated by reference in their entirety.

Methods based on ligation of two (or more) oligonucleotides in the presence of nucleic acid having the sequence of the resulting "di-oligonucleotide", thereby amplifying the di-oligonucleotide, also may be used in the amplification step of the present invention. Wu et al. (1989), incorporated herein by reference in its entirety.

4.5.3 Separation Methods

Following amplification, it may be desirable to separate the amplification product from the template and the excess primer for the purpose of determining whether specific amplification has occurred. In one embodiment, amplification products are separated by agarose, agarose-acrylamideor polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

4.5.4 Identification Methods

Amplification products must be visualized in order to confirm amplification of the target nucleic acid sequences. One typical visualization method involves staining of a gel with ethidium bromide and visualization under UV light. Alternatively, if the amplification products are integrally labeled with radio- or fluorometrically-labeled nucleotides, the amplification products may then be exposed to x-ray film or visualized under the appropriate stimulating spectra, following separation.

In one embodiment, visualization is achieved indirectly. Following separation of amplification products, a labeled, nucleic acid probe is brought into contact with the amplified target nucleic acid sequence. The probe preferably is conjugated to a chromophore but may be radiolabeled. In another embodiment, the probe is conjugated to a binding partner, such as an antibody or biotin, where the other member of the binding pair carries a detectable moiety.

In one embodiment, detection is by Southern blotting and hybridization with a labeled probe. The techniques involved in Southern blotting are well known to those of skill in the art and may be found in many standard books on molecular protocols. See Sambrook et al., 1989. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

4.5.5 Kit Components

All the essential materials and reagents required for detecting UC41 nucleic acids in a biological sample may be assembled together in a kit. The kit generally will comprise preselected primer pairs for nucleic acids corresponding to SEQ ID NO:1, SEQ ID NO:3 or SEQ ID NO:4. Also included may be enzymes suitable for amplifying nucleic acids including various polymerases (RT, Taq, etc.), deoxynucleotides and buffers to provide the necessary reaction mixture for amplification. Preferred kits also may comprise primers for the detection of a control, non-differentially expressed RNA such as β-actin, for example.

The kits generally will comprise, in suitable means, distinct containers for each individual reagent and enzyme as well as for each primer pair. Preferred pairs of primers for amplifying nucleic acids are selected to amplify the sequences designated herein as SEQ ID NO: 1, SEQ ID NO:3 or SEQ ID NO:4.

In certain embodiments, kits will comprise hybridization probes designed to hybridize to a sequence or a complement of a sequence designated herein as SEQ ID NO: 1, SEQ ID NO:3 or SEQ ID NO:4. Such kits generally will comprise, in suitable means for close confinement, distinct containers for each individual reagent and enzyme as well as for each hybridization probe.

4.6 Use of RNA Fingerprinting

RNA fingerprinting is a means by which RNAs isolated from many different tissues, cell types or treatment groups may be sampled simultaneously to identify RNAs whose relative abundances vary. Two forms of this technology were developed simultaneously and reported in 1992 as RNA fingerprinting by differential display (Liang and Pardee, 1992; Welsh et al., 1992). (See also Liang and Pardee, U.S. Pat. No. 5,262,311, incorporated herein by reference in its entirety.) Both techniques were utilized in the studies described below. Some of the studies described herein were performed similarly to Donahue et al., 1994.

The basic technique of differential display has been described in detail (Liang and Pardee, 1992). Total cell RNA is primed for first strand reverse transcription with an anchoring primer composed of oligo dT. The oligo dT primer is extended using a reverse transcriptase, for example, Moloney Murine Leukemia Virus (MMLV) reverse transcriptase. The synthesis of the second strand is primed with an arbitrarily chosen oligonucleotide, using reduced stringency conditions. Once the double-stranded cDNA has been synthesized, amplification proceeds by standard PCR™ techniques, utilizing the same primers. The resulting DNA fingerprint is analyzed by gel electrophoresis and ethidium bromide staining or autoradiography. A side by side comparison of fingerprints obtained from different cell derived RNAs using the same oligonucleotide primers identifies mRNAs that are differentially expressed.

RNA fingerprinting technology has been demonstrated as being effective in identifying genes that are differentially expressed in cancer (Liang et al., 1992; Wong et al., 1993; Sager et al., 1993; Mok et al., 1994; Watson et al., 1994; Chen et al., 1995a; Chen et al., 1995b; An et al., 1995). The present invention utilizes the RNA fingerprinting technique to identify genes that are differentially expressed in prostate, cancer. These studies utilized RNAs isolated from tumor tissues and tumor-derived cell lines that behave as tumors cells with different metastatic potential.

The underlying concept of these studies was that genes that are differentially expressed in cells with different metastatic potentials may be used as indicators of metastatic potential. Since metastasis is a prerequisite for prostate, cancer progression to life threatening pathologies, indicators of metastatic potential are likely to be indicators of pathological potential.

Reverse transcription (RT) of RNA to cDNA followed by relative quantitative PCR™ (RT-PCR™) may be used to determine the relative concentrations of specific mRNA species in a series of total cell RNAs isolated from normal., benign and cancerous prostate, tissues. By determining that the concentration of a specific mRNA species varies, it is shown that the gene encoding the specific mRNA species is differentially expressed. This technique may be used to confirm that mRNA transcripts shown to be differentially regulated by RNA fingerprinting are differentially expressed in prostate, cancer progression.

The problems inherent in clinical samples are that they are of variable quantity (making normalization problematic), and that they are of variable quality (necessitating the co-amplification of a reliable internal control, preferably of larger size than the target).

Both of these problems are overcome if the RT-PCR™ is performed as a relative quantitative RT-PCR™ with an internal standard in which the internal standard is an amplifiable cDNA fragment that is larger than the target cDNA fragment and in which the abundance of the mRNA encoding the internal standard is roughly 5–100 fold higher than the mRNA encoding the target. This assay measures relative abundance, not absolute abundance of the respective mRNA species.

Other studies described below were performed using a more conventional relative quantitative RT-PCR™ with an external standard protocol. These assays sample the PCR™ products in the linear portion of their amplification curves. The number of PCR™ cycles that are optimal for sampling must be empirically determined for each target cDNA fragment. In addition, the reverse transcriptase products of each RNA population isolated from the various tissue samples must be carefully normalized for equal concentrations of amplifiable cDNAs. This is very important since this assay measures absolute mRNA abundance. Absolute mRNA abundance may be used as a measure of differential gene expression only in normalized samples. While empirical determination of the linear range of the amplification curve and normalization of cDNA preparations are tedious and time consuming processes, the resulting RT-PCR™ assays may be superior to those derived from the relative quantitative RT-PCR™ with an internal standard.

One reason for this is that without the internal standard/ competitor, all of the reagents may be converted into a single PCR™ product in the linear range of the amplification curve, increasing the sensitivity of the assay. Another reason is that with only one PCR™ product, display of the product on an electrophoretic gel or some other display method becomes less complex, has less background and is easier to interpret.

4.7 Diagnosis and Prognosis of Human Cancer

In certain embodiments, the present invention allows the diagnosis and prognosis of human prostate cancer by screening for prostate specific nucleic acids, particularly those that are overexpressed in prostate cancer. The field of cancer diagnosis and prognosis is still uncertain. Various markers have been proposed to be correlated with metastasis and malignancy. They may be classified generally as cytologic, protein or nucleic acid markers.

Cytologic markers include such things as "nuclear roundedness" (Diamond et al., 1982) and cell ploidy. Protein markers include prostate specific antigen (PSA) and CA125. Nucleic acid markers have included amplification of Her2/neu, point mutations in the p53 or ras genes, and changes in the sizes of triplet repeat segments of particular chromosomes.

All of these markers exhibit certain drawbacks, associated with false positives and false negatives. A false positive result occurs when an individual without malignant cancer exhibits the presence of a "cancer marker". For example, elevated serum PSA has been associated with prostate carcinoma. However, it also occurs in some individuals with non-malignant, benign hyperplasia of the prostate. A false negative result occurs when an individual actually has cancer, but the test fails to show the presence of a specific marker. The incidence of false negatives varies for each marker, and frequently also by tissue type. For example, ras point mutations have been reported to range from a high of 95 percent in pancreatic cancer to a low of zero percent in some gynecologic cancers.

Additional problems arise when a marker is present only within the transformed cell itself. Ras point mutations may only be detected within the mutant cell, and are apparently not present in, for example, the blood serum or urine of individuals with ras-activated carcinomas. This means that, in order to detect a malignant tumor, one must take a sample of the tumor itself, or its metastatic cells. Since the object of cancer detection is to identify and treat tumors before they metastasize, essentially one must first identify and sample a tumor before the presence of the cancer marker can be detected.

Finally, specific problems occur with markers that are present in normal cells but absent in cancer cells. Most tumor samples will contain mixed populations of both normal and transformed cells. If one is searching for a marker that is present in normal cells, but occurs at reduced levels in transformed cells, the "background" signal from the normal cells in the sample may mask the presence of transformed cells.

The ideal cancer marker would be one that is present in malignant cancers, and either missing or else expressed at significantly lower levels in benign tumors and normal cells. The present invention addresses this need for prostate cancer markers by identifying a novel, prostate specific gene (UC Band #41) which is expressed at much higher levels in malignant prostate carcinoma than in benign or normal prostate. In particular, the results for UC Band #41 (SEQ ID NO: 1, SEQ ID NO:3 and SEQ ID NO:4) discussed in Examples 1–5 below, are quite promising in that this marker is apparently only overexpressed in malignant tumors and is present at very low levels in BPH or normal prostate.

Further, this gene is significantly elevated in a high percentage of human prostate cancers examined to date.

It is expected that in clinical applications, human tissue samples will be screened for the presence of the expression products of UC41. Such samples could consist of needle biopsy cores, surgical resection samples, lymph node tissue, or serum. In certain embodiments, nucleic acids would be extracted from these samples and amplified as described above. Some embodiments would utilize kits containing pre-selected primer pairs or hybridization probes. The amplified nucleic acids would be tested for UC41 expression products by, for example, gel electrophoresis and ethidium bromide staining, or Southern blotting, or a solid-phase detection means as described above. These methods are well known within the art. The levels of expression product(s) detected would be compared with statistically valid groups of metastatic, non-metastatic malignant, benign or normal prostate samples. The diagnosis and prognosis of the individual patient would be determined by comparison with such groups.

Another embodiment of the present invention involves application of RT-PCR™ techniques to detect circulating prostate cancer cells (i.e., those that have already metastasized), using probes and primers selected from sequences or their complements designated herein as SEQ ID NO: 1, SEQ ID NO:3 or SEQ ID NO:4. Similar techniques have been described in PCT Patent Application No. WO 94/10343, incorporated herein by reference.

In this embodiment, metastatic prostate cancer cells are detected in hematopoietic samples by amplification of prostate cancer-specific nucleic acid sequences. Samples taken from blood or lymph nodes are treated as described below to purify total cell RNA. The isolated RNA is reverse transcribed using a reverse transcriptase and primers selected to bind under high stringency conditions to a nucleic acid sequence to the sequence of SEQ ID NO:1, SEQ ID NO:3 or SEQ ID NO:4. Following reverse transcription, the resulting cDNAs are amplified using standard PCR™ techniques (described below) and a thermostable DNA polymerase.

The presence of amplification products corresponding to UC41 nucleic acids may be detected by several alternative means. In one embodiment, the amplification product may be detected by gel electrophoresis and ethidium bromide staining. Alternatively, following the gel electrophoresis step the amplification product may be detected by standard Southern blotting techniques, using an hybridization probe selected to bind specifically to a nucleic acid corresponding to SEQ ID NO:1, SEQ ID NO:3 or SEQ ID NO:4. Probe hybridization may in turn be detected by a standard labeling means, for example, by incorporation of [$^{32}$P]-nucleotides followed by autoradiography. The amplification products may alternatively be detected using a solid phase detection system as described above, utilizing a hybridization probe specific for SEQ ID NO: 1, SEQ ID NO:3 or SEQ ID NO:4 and an appropriate labeling means. The presence of UC41 nucleic acids in blood or lymph node samples may be taken as indicative of a patient with metastatic prostate cancer.

4.8 Targeted Inhibition of A Prostate Specific Gene

In principal., the novel prostate specific gene (UC41) identified in the present invention may serve as a target for therapeutic intervention in prostate cancer.

Inhibitors could potentially be designed for UC41. This is complicated by the fact that no specific function has been identified for this gene products, and no data is available on its three-dimensional structures.

Identification of protein function may be extrapolated, in some cases, from the primary sequence data, provided that sequence homology exists between the unknown protein and a protein of similar sequence and known function. Proteins tend to occur in large families of relatively similar sequence and function. For example, a number of the serine proteases, like trypsin and chymotrypsin, have extensive sequence homologies and relatively similar three-dimensional structures. Other general categories of homologous proteins include different classes of transcriptional factors, membrane receptor proteins, tyrosine kinases, GTP-binding proteins, etc. The putative amino acid sequences encoded by the prostate specific gene of the present invention may be cross-checked for sequence homologies versus the protein sequence database of the National Biomedical Research Fund. Homology searches are standard techniques for the skilled practitioner.

Even three-dimensional structure may be inferred from the primary sequence data of the encoded protein(s). Again, if homologies exist between the encoded amino acid sequences and other proteins of known structure, then a model for the structure of the encoded protein may be designed, based upon the structure of the known protein. An example of this type of approach was reported by Ribas de Pouplana and Fothergill-Gilmore (1994). These authors developed a detailed three-dimensional model for the structure of Drosophila alcohol dehydrogenase, based in part upon sequence homology with the known structure of 3-α, 20-β-hydroxysteroiddehydrogenase. Once a three-dimensional model is available, inhibitors may be designed by standard computer modeling techniques. This area has been reviewed by Sun and Cohen (1993), herein incorporated by reference.

4.8.1 Antisense constructs

The term "antisense" is intended to refer to polynucleotide molecules complementary to a portion of an RNA expression product of UC41, as defined herein. "Complementary" polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal., including a human subject.

The intracellular concentration of monovalent cation is approximately 160 mM (10 mM $Na^+$; 150 mM $K^+$). The intracellular concentration of divalent cation is approximately 20 mM (18 mM $Mg^+$; 2 mM $Ca^{++}$). The intracellular protein concentration, which would serve to decrease the volume of hybridization and, therefore, increase the effective concentration of nucleic acid species, is 150 mg/ml. Constructs can be tested in vitro under conditions that mimic these in vivo conditions.

Antisense constructs may be designed to bind to the promoter and other control regions, exons, introns or even exon-intron boundaries of a gene. It is contemplated that the most effective antisense constructs for the present invention will include regions complementary to the mRNA start site, or to those sequences identified herein as SEQ ID NO:1, SEQ ID NO:3 or SEQ ID NO:4. One can readily test such constructs simply by testing the constructs in vitro to determine whether levels of the target protein are affected. Similarly, detrimental non-specific inhibition of protein synthesis also can be measured by determining target cell viability in vitro.

As used herein, the terms "complementary" or "antisense" mean polynucleotides that are substantially complementary over their entire length and have very few base mismatches. For example, sequences of fifteen bases in length may be termed complementary when they have a complementary nucleotide at thirteen or fourteen nucleotides out of fifteen. Naturally, sequences which are "completely complementary" will be sequences which are entirely complementary throughout their entire length and have no base mismatches.

Other sequences with lower degrees of homology also are contemplated. For example, an antisense construct which has limited regions of high homology, but also contains a non-homologous region (e.g., a ribozyme) could be designed. These molecules, though having less than 50% homology, would bind to target sequences under appropriate conditions.

As stated above, although the antisense sequences may be full length cDNA copies, or large fragments thereof, they also may be shorter fragments, or "oligonucleotides," defined herein as polynucleotides of 50 or less bases. Although shorter oligomers (8–20) are easier to make and increase in vivo accessibility, numerous other factors are involved in determining the specificity of base-pairing. For example, both binding affinity and sequence specificity of an oligonucleotide to its complementary target increase with increasing length. It is contemplated that oligonucleotides of 8, 9, 10, 11, 12, 13, 14, 15, 16, 17, 18, 19, 20, 25, 30, 35, 40, 45, 50 or 100 base pairs will be used. While all or part of the gene sequence may be employed in the context of antisense construction, statistically, any sequence of 14 bases long should occur only once in the human genome and, therefore, suffice to specify a unique target sequence.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

As an alternative to targeted antisense delivery, targeted ribozymes may be used. The term "ribozyme" is refers to an RNA-based enzyme capable of targeting and cleaving particular base sequences in both DNA and RNA. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cell lines to which they were applied; the altered genes included the oncogenes H-ras, c-fos and genes of HIV. Most of this work involved the modification of a target mRNA, based on a specific mutant codon that is cleaved by a specific ribozyme.

Ribozymes can either be targeted directly to cells, in the form of RNA oligonucleotides incorporating ribozyme sequences, or introduced into the cell as an expression vector encoding the desired ribozymal RNA. Ribozymes may be used and applied in much the same way as described for antisense polynucleotide. Ribozyme sequences also may be modified in much the same way as described for antisense polynucleotide. For example, one could incorporate non-Watson-Crick bases, or make mixed RNA/DNA oligonucleotides, or modify the phosphodiester backbone, or modify the 2'-hydroxy in the ribose sugar group of the RNA.

Alternatively, the antisense oligo- and polynucleotides according to the present invention may be provided as RNA via transcription from expression constructs that carry nucleic acids encoding the oligo- or polynucleotides. Throughout this application, the term "expression construct" is meant to include any type of genetic construct containing a nucleic acid encoding an antisense product in which part or all of the nucleic acid sequence is capable of being transcribed. Typical expression vectors include bacterial plasmids or phage, such as any of the pUC or Bluescript™ plasmid series or, as discussed further below, viral vectors adapted for use in eukaryotic cells.

In preferred embodiments, the nucleic acid encodes an antisense oligo- or polynucleotide under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid encoding the inhibitory peptide is not believed to be important, so long as it is capable of expressing the peptide in the targeted cell. Thus, where a human cell is targeted, it is preferable to position the nucleic acid coding the inhibitory peptide adjacent to and under the control of a promoter that is active in the human cell. Generally speaking, such a promoter might include either a human or viral promoter.

In various embodiments, the human cytomegalovirus (CMV) immediate early gene promoter, the SV40 early promoter and the Rous sarcoma virus long terminal repeat can be used to obtain high-level expression of various proteins. The use of other viral or mammalian cellular or bacterial phage promoters which are well-known in the art to achieve expression of peptides according to the present invention is contemplated as well, provided that the levels of expression are sufficient for a given purpose.

By employing a promoter with well-known properties, the level and pattern of expression of an antisense oligo- or polynucleotide can be optimized. Further, selection of a promoter that is regulated in response to specific physiologic signals can permit inducible expression of an inhibitory protein. For example, a nucleic acid under control of the human PAI-1 promoter results in expression inducible by tumor necrosis factor. Additionally any promoter/enhancer combination (as per the Eukaryotic Promoter Data Base EPDB) also could be used to drive expression of a nucleic acid according to the present invention. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Tables 2 and 3 list several elements/promoters which may be employed, in the context of the present invention, to regulate the expression of the gene of interest. This list is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers, and inducible promoters/enhancers that could be used in combination with the nucleic acid encoding a gene of interest in an expression construct (Table 2 and Table 3).

Additionally, any promoter/enhancer combination (as per the Eukaryotic Promoter Data Base EPDB) also could be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 2

| ENHANCER/PROMOTER |
| --- |
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DRα |
| β-Actin |
| Prealbumin (Transthyretin) |
| Muscle Creatine Kinase |
| Elastase I |
| Metallothionein |
| Collagenase |
| Albumin Gene |
| α-Fetoprotein |
| τ-Globin |
| β-Globin |
| e-fos |
| c-HA-ras |
| Insulin |
| Neural Cell Adhesion Molecule (NCAM) |
| α1-Antitrypsin |
| H2B (TH2B) Histone |
| Mouse or Type I Collagen |
| Glucose-Regulated Proteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV4O |
| Polyoma |
| Retroviruses |
| Papilloma Virus |
| Hepatitis B Virus |
| Human Immunodeficiency Virus |
| Cytomegalovirus |

TABLE 3

| Element | Inducer |
| --- | --- |
| MT II | Phorbol Ester (TPA) |
| | Heavy metals |
| MMTV (mouse mammary tumor virus) | Glucocorticoids |
| β-Interferon | poly(rI)X, poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV4O | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV4O Large T Antigen |
| Proliferin | Phorbol Ester-TPA |
| Tumor Necrosis Factor | FMA |
| Thyroid Stimulating Hormone α Gene | Thyroid Hormone |
| Insulin E Box | Glucose |

Where a cDNA insert is employed, typically one will typically include a polyadenylation signal to effect proper polyadenylation of the gene transcript. The nature of the polyadenylation signal is not believed to be crucial to the successful practice of the invention, and any such sequence may be employed, such as human growth hormone and SV40 polyadenylation signals. Also contemplated as an element of the expression construct is a terminator. These elements can serve to enhance message levels and to minimize read through from the construct into other sequences.

In certain embodiments of the invention, the delivery of a nucleic acid in a cell may be identified in vitro or in vivo by including a marker in the expression construct. The marker would result in an identifiable change to the transfected cell permitting identification of expression. Enzymes such as herpes simplex virus thymidine kinase (tk) (eukaryotic) or chloramphenicol acetyltransferase (CAT) (prokaryotic) may be employed.

One also may include a polyadenylation signal to effect proper polyadenylation of the transcript. The nature of the polyadenylation signal is not believed to be crucial to the successful practice of the invention, and any such sequence may be employed. For example, the SV40, β-globin or adenovirus polyadenylation signal may be employed. Also contemplated as an element of the expression cassette is a terminator. These elements can serve to enhance message levels and to minimize read through from the cassette into other sequences.

4.8.2 Single-chain Antibodies

In yet another embodiment, one gene may comprise a single-chain antibody. Methods for the production of single-chain antibodies are well known to those of skill in the art. The skilled artisan is referred to U.S. Pat. No. 5,359,046, (incorporated herein by reference) for such methods. A single chain antibody is created by fusing together the variable domains of the heavy and light chains using a short peptide linker, thereby reconstituting an antigen binding site on a single molecule.

Single-chain antibody variable fragments (scFvs) in which the C-terminus of one variable domain is tethered to the N-terminus of the other via a 15 to 25 amino acid peptide or linker, have been developed without significantly disrupting antigen binding or specificity of the binding (Bedzyk et al., 1990; Chaudhary et al., 1990). These Fvs lack the constant regions (Fc) present in the heavy and light chains of the native antibody. Single-chain antibodies to the protein products of the UC41 gene are contemplated within the scope of the present invention.

Single-chain antibodies can be synthesized by a cell, targeted to particular cellular compartments, and used to interfere in a highly specific manner with cell growth and metabolism. Recently, single-chain antibodies were utilized for the phenotypic knockout of growth-factor receptors, the functional inactivation of p21ras, and the inhibition of HIV-1 replication. Intracellular antibodies offer a simple and effective alternative to other forms of gene inactivation, as well as demonstrate a clear potential as reagents for cancer therapy and for the control of infectious diseases. Single-chain antigen-binding proteins also represent potentially unique molecules for targeted delivery of drugs, toxins, or radionuclides to a tumor site, and show increased accessibility to tumor cells in vivo (Yokoda et al., 1992).

It is also contemplated by the present invention that single-chain antibody therapy can be combined with chemotherapeutic or radiotherapeutic intervention. The discussion of combined therapy with traditional chemotherapy or radiotherapy employed herein is incorporated into this section by reference.

4.8.3 Liposomal formulations

In certain broad embodiments of the invention, the antisense oligo- or polynucleotides and/or expression vectors may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are cationic lipid-nucleic acid complexes, such as lipofectamine-nucleic acid complexes.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression vectors have been successfully employed in transfer and expression of a polynucleotide in vitro and in vivo, then they are applicable for the present invention. Where a bacterial promoter is employed in the DNA construct, it also will be desirable to include within the liposome an appropriate bacterial polymerase. "Liposome" is a generic term encompassing a variety of single and multilamellar lipid vehicles formed by the generation of enclosed lipid bilayers. Phospholipids are used for preparing the liposomes according to the present invention and can carry a net positive charge, a net negative charge or are neutral. Dicetyl phosphate can be employed to confer a negative charge on the liposomes, and stearylamine can be used to confer a positive charge on the liposomes.

Lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem (La Jolla, Calif.); dimyristyl phosphatidylglycerol ("DMPG") and other lipids may be obtained from Avanti Polar Lipids, Inc. (Birmingham, Ala.). Stock solutions of lipids in chloroform, chloroform/methanol or t-butanol can be stored at about −20° C. Preferably, chloroform is used as the only solvent since it is more readily evaporated than methanol.

Phospholipids from natural sources, such as egg or soybean phosphatidylcholine, brain phosphatidic acid, brain or plant phosphatidylinositol, heart cardiolipin and plant or bacterial phosphatidylethanolamineare preferably not used as the primary phosphatide, i.e., constituting 50% or more of the total phosphatide composition, because of the instability and leakiness of the resulting liposomes.

Liposomes used according to the present invention can be made by different methods. The size of the liposomes varies depending on the method of synthesis. A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules will form a bilayer, known as a lamella, of the arrangement XY-YX.

Liposomes within the scope of the present invention can be prepared in accordance with known laboratory techniques. In one preferred embodiment, liposomes are prepared by mixing liposomal lipids, in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min to 2 h, depending on the desired volume of the liposomes. The composition can be dried further in a desiccator under vacuum. The dried lipids generally are discarded after about 1 wk because of a tendency to deteriorate with time.

Dried lipids can be hydrated at approximately 25–50 mM phospholipid in sterile, pyrogen-free water by shaking until all the lipid film is resuspended. The aqueous liposomes can be then separated into aliquots, each placed in a vial., lyophilized and sealed under vacuum.

In the alternative, liposomes can be prepared in accordance with other known laboratory procedures: the method of Bangham et al. (1965), the contents of which are incorporated herein by reference; the method of Gregoriadis, as described in *DRUG CARRIERS IN BIOLOGYAND MEDICINE*, G. Gregoriadis (1979), the contents of which are incorporated herein by reference; the method of Deamer and Uster (1983), the contents of which are incorporated by reference; and the reverse-phase evaporation method as described by Szoka and Papahadjopoulos (1978). The aforementioned methods differ in their respective abilities to entrap aqueous material and their respective aqueous space-to-lipid ratios.

The dried lipids or lyophilized liposomes prepared as described above may be reconstituted in a solution of nucleic acid and diluted to an appropriate concentration with an suitable solvent, e.g., DPBS. The mixture is then vigorously shaken in a vortex mixer. Unencapsulated nucleic acid is removed by centrifugation at 29,000×g and the liposomal pellets washed. The washed liposomes are resuspended at an appropriate total phospholipid concentration, e.g, about 50–200 mM. The amount of nucleic acid encapsulated can be determined in accordance with standard methods. After determination of the amount of nucleic acid encapsulated in the liposome preparation, the liposomes may be diluted to appropriate concentration and stored at 4° C. until use.

In a preferred embodiment, the lipid dioleoylphosphatidylcholine is employed. Nuclease-resistant oligonucleotides were mixed with lipids in the presence of excess t-butanol. The mixture was vortexed before being frozen in an acetone/dry ice bath. The frozen mixture was lyophilized and hydrated with Hepes-buffered saline (1 mM Hepes, 10 mM NaCl, pH 7.5) overnight, and then the liposomes were sonicated in a bath type sonicator for 10 to 15 min. The size of the liposomal-oligonucleotides typically ranged between 200–300 nm in diameter as determined by the submicron particle sizer autodilute model 370 (Nicomp, Santa Barbara, Calif.).

4.8.4 Viral Delivery Systems

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into a host cell genome, and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). Preferred gene therapy vectors are generally viral vectors.

Although some viruses that can accept foreign genetic material are limited in the number of nucleotides they can accommodate and in the range of cells they infect, these viruses have been demonstrated to successfully effect gene expression. However, adenoviruses do not integrate their genetic material into the host genome and therefore do not require host replication for gene expression making them ideally suited for rapid, efficient, heterologous gene expression. Techniques for preparing replication infective viruses are well known in the art.

Of course in using viral delivery systems, one will desire to purify the virion sufficiently to render it essentially free of undesirable contaminants, such as defective interfering viral particles or endotoxins and other pyrogens such that it will not cause any untoward reactions in the cell, animal or individual receiving the vector construct. A preferred means of purifying the vector involves the use of buoyant density gradients, such as cesium chloride gradient centrifugation.

Viruses used as gene vectors such as DNA viruses may include the papovaviruses (e.g., simian virus 40, bovine papilloma virus, and polyoma) (Ridgeway, 1988; Baichwal and Sugden, 1986) and adenoviruses (Ridgeway, 1988; Baichwal and Sugden, 1986).

One of the preferred methods for in vivo delivery involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to express an antisense polynucleotide that has been cloned therein.

The expression vector comprises a genetically engineered form of adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retroviral infection, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNAs issued from this promoter possess a 5'-tripartite leader (TPL) sequence which makes them preferred mRNAs for translation.

In currently used systems, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of adenovirus vectors which are replication deficient depend on a unique helper cell line, designated 293, which is transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the E3, or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells, may be derived from the cells of other mammalian species that are permissive for human adenovirus. Such cells include, e.g., Vero cells or other monkey embryonic mesenchymal or epithelial cells. As discussed, the preferred helper cell line is 293.

Recently, Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) are employed as follows. A cell innoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking is initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking is commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

A typical vector applicable to practicing the present invention is replication defective and will not have an adenovirus E1 region. Thus, it will be most convenient to introduce the polynucleotide encoding the UC41 gene at the position from which the E1-coding sequences have been removed. However, the position of insertion of the construct within the adenovirus sequences is not critical. The polynucleotide encoding the UC41 gene also may be inserted in lieu of the deleted E3 region in E3 replacement vectors as described by Karlsson et al., (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

Other gene transfer vectors may be constructed from retroviruses. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env. that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences, and also are required for integration in the host cell genome (Coffin, 1990).

In order to construct a retroviral vector, a nucleic acid encoding a UC41 gene is inserted into the viral genome in the place of certain viral sequences to produce a virus that is replication-defective. In order to produce virions, a packaging cell line containing the gag, pol, and env genes, but without the LTR and packaging components, is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are capable of infecting a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses has been designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, the infection of a variety of human cells that bear those surface antigens with an ecotropic virus in vitro was demonstrated (Roux et al., 1989).

There are certain limitations to the use of retrovirus vectors. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This may result from recombination events in which the intact sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Other viral vectors may be employed as expression constructs. Vectors derived from viruses such as vaccinia virus (Ridgeway, 1988; Baichwal and Sugden, 1986; Coupar et al., 1988), adeno-associated virus (AAV) (Ridgeway, 1988; Baichwal and Sugden, 1986; Hermonat and Muzycska, 1984) and herpes viruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight has been gained into the structure-finction relationship of different viral sequences. In vitro studies showed that the virus could retain the ability for helper-dependent packaging and reverse transcription despite the deletion of up to 80% of its genome (Horwich et al., 1990). This suggests that large portions of the genome can be replaced with foreign genetic material. The hepatotropism and persistence (integration) are particularly attractive properties for liver-directed gene transfer. Chang et al. (1991) recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

To effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

4.8.5 Non-viral Methods

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990), DEAE-dextran (Gopal., 1985), electroporation (Tur-Kaspa et al., 1986; Potter et al.,1984) direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

In one embodiment of the invention, the expression construct may simply consist of naked recombinant vector. Transfer of the construct may be performed by any of the methods mentioned above which physically or chemically permeabilize the cell membrane. For example, Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding an antisense UC41 construct also may be transferred in a similar manner in vivo.

Once the expression construct has been delivered into the cell the nucleic acid encoding the UC41 gene may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

4.8.6 Pharmaceutical Compositions and Routes of Administration

Where clinical application of liposomes containing antisense oligo- or polynucleotides or expression vectors is undertaken, it will be necessary to prepare the liposome complex as a pharmaceutical composition appropriate for the intended application. Generally, this will entail preparing a pharmaceutical composition that is essentially free of pyrogens, as well as any other impurities that could be harmful to humans or animals. One also will generally desire to employ appropriate buffers to render the complex stable and allow for uptake by target cells.

Aqueous compositions of the present invention comprise an effective amount of the antisense expression vector encapsulated in a liposome as discussed above, further dispersed in pharmaceutically acceptable carrier or aqueous medium. Such compositions also are referred to as innocula. The phrases "pharmaceutically or pharmacologically acceptable" refer to compositions that do not produce an adverse, allergic or other untoward reaction when administered to an animal., or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present invention are advantageously administered in the form of injectable compositions either as liquid solutions or suspensions; solid forms suitable for solution in, or suspension in, liquid prior to injection also may be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting dose include physical and clinical state of the patient, the route of administration and the potency, stability and toxicity of the particular therapeutic substance. For the instant application, it is envisioned that the amount of therapeutic composition comprising a unit dose will range from about 5–30 mg of polynucleotide.

4.9 Methods for Treating UC41 Related Malignancies

The present invention also contemplates, in another embodiment, the treatment of prostate cancer. The types of cancer that may be treated, according to the present invention, are limited only by the involvement of UC41. By involvement is meant that, it is not even a requirement that UC41 be mutated or abnormal—the overexpression or underexpression of the protein(s) encoded by this gene may be a primary factor in the development of prostate cancer. Thus, it is contemplated that tumors may be treated using antisense or expression therapy targeted to the UC41 gene product(s).

In many contexts, it is not necessary that the tumor cell be killed or induced to undergo normal cell death or "apoptosis." Rather, to accomplish a meaningful treatment, all that is required is that the tumor growth be slowed to some degree. It may be that the tumor growth is completely blocked, however, or that some tumor regression is achieved. Clinical terminology such as "remission" and "reduction of tumor" burden also are contemplated given their normal usage.

4.9.1 Genetic Based Therapies

One of the therapeutic embodiments contemplated by the present inventors is the intervention, at the molecular level, in the events involved in the tumorigenesis of some cancers. Specifically, the present inventors intend to provide, to a cancer cell, an antisense construct capable of inhibiting expression of UC41 in that cell. Particularly preferred expression vectors are viral vectors such as adenovirus, adeno-associated virus, herpes virus, vaccinia virus and retrovirus. Also preferred is liposomally-encapsulated expression vector.

Those of skill in the art are well aware of how to apply gene delivery to in vivo and ex vivo situations. For viral vectors, one generally will prepare a viral vector stock. Depending on the kind of virus and the titer attainable, one will deliver between about $1 \times 10^4$ and $1 \times 10^{12}$ infectious particles to the patient. Similar figures may be extrapolated for liposomal or other non-viral formulations by comparing relative uptake efficiencies. Formulation as a pharmaceutically acceptable composition is discussed below.

Various routes are contemplated for various tumor types. The section below on routes contains an extensive list of possible routes. For practically any tumor, systemic delivery is contemplated. This will prove especially important for attacking microscopic or metastatic cancer. Where discrete tumor mass may be identified, a variety of direct, local and regional approaches may be taken. For example, the tumor may be injected directly with the expression vector. A tumor bed may be treated prior to, during or after resection. Following resection, one generally will deliver the vector by a catheter left in place following surgery. One may utilize the tumor vasculature to introduce the vector into the tumor by injecting a supporting vein or artery. A more distal blood supply route also may be utilized.

In a different embodiment, ex vivo gene therapy is contemplated. This approach is particularly suited, although not limited, to treatment of bone marrow associated cancers. In an ex vivo embodiment, cells from the patient are removed and maintained outside the body for at least some period of time. During this period, a therapy is delivered, after which the cells are reintroduced into the patient. Preferably, any tumor cells in the sample have been killed.

4.9.2 Immunotherapies

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

According to the present invention, native or wild type UC41 may be a target for an immune effector. It is possible UC41 may be targeted by immunotherapy, either using antibodies, antibody conjugates, or immune effector cells.

Alternatively, immunotherapy could be used as part of a combined therapy, in conjunction with UC41-targeted gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, sialyl Lewis antigen, MucA, MucB, PLAP, estrogen receptor, laminin receptor, erb B and p155.

4.9.3 Combined Therapy with Immunotherapy, Chemotherapy or Radiotherapy

Tumor cell resistance to DNA damaging agents represents a major problem in clinical oncology. One goal of current cancer research is to find ways to improve the efficacy of chemo- and radiotherapy. One way is by combining such traditional therapies with gene therapy. For example, the herpes simplex-thymidine kinase (HS-tk) gene, when delivered to brain tumors by a retroviral vector system, successfully induced susceptibility to the antiviral agent ganciclovir (Culver et al., 1992). In the context of the present invention, it is contemplated that UC41 gene therapy could be used similarly in conjunction with chemo- or radiotherapeutic intervention.

To kill cells, inhibit cell growth, inhibit metastasis, inhibit angiogenesis or otherwise reverse or reduce the malignant phenotype of tumor cells, using the methods and compositions of the present invention, one would generally contact a "target" cell with an antisense construct of UC41 and at least one other agent. These compositions would be provided in a combined amount effective to kill or inhibit proliferation of the cell. This process may involve contacting the cells with the antisense construct and the agent(s) or factor(s) at the same time. This may be achieved by contacting the cell with a single composition or pharmacological formulation that includes both agents, or by contacting the cell with two distinct compositions or formulations simultaneously, wherein one composition includes the antisense or expression construct and the other includes the agent.

Alternatively, the gene therapy treatment may precede or follow the other agent treatment by intervals ranging from min to wk. In embodiments where the other agent and expression construct are applied separately to the cell, one would generally ensure that a significant period of time did not expire between the time of each delivery, such that the agent and expression construct would still be able to exert an advantageously combined (e.g., synergistic) effect on the cell. In such instances, it is contemplated that one would contact the cell with both modalities within about 12–24 h of each other and, more preferably, within about 6–12 h of each other, with a delay time of only about 12 h being most preferred. In some situations, it may be desirable to extend the duration of treatment with only the therapeutic agent significantly, for example, where several days (2, 3, 4, 5, 6 or 7) to several wk (1, 2, 3, 4, 5, 6, 7 or 8) lapse between the respective administrations.

It also is conceivable that more than one administration of either UC41 antisense construct or the other agent will be desired. Various combinations may be employed, where UC41 is "A" and the other agent is "B", as exemplified below:

A/B/A B/A/B B/B/A A/A/B B/A/A A/B/B B/B/B/A B/B/A/B

A/A/B A/B/A/B A/B/B/A B/B/A/A B/A/B/A B/A/A/B B/B/B/A

A/A/A/B B/A/A/A AIB/A/A A/A/B/A A/B/B/B B/A/B/B B/B/A/B

To achieve cell killing, both agents are delivered to a cell in a combined amount effective to kill the cell.

Agents or factors suitable for use in a combined therapy are any chemical compound or treatment method that induces DNA damage when applied to a cell. Such agents and factors include radiation and waves that induce DNA damage such as γ-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeuticagents contemplated to be of use include, e.g., adriamycin, 5-fluorouracil (5FU), etoposide (VP-16), camptothecin, actinomycin-D, mitomycinC, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide.

In treating cancer according to the invention, one would contact the tumor cells with an agent in addition to the antisense construct. This may be achieved by irradiating the localized tumor site with radiation such as X-rays, UV-light, γ-rays or even microwaves. Alternatively, the tumor cells may be contacted with the agent by administering to the subject a therapeutically effective amount of a pharmaceutical composition comprising a compound such as, adriamycin, 5-fluorouracil, etoposide, camptothecin, actinomycin-D, or mitomycin C. The agent may be prepared and used as a combined therapeutic composition, or kit, by combining it with a UC41 antisense construct, as described above.

Agents that directly cross-link nucleic acids, specifically DNA, are envisaged to facilitate DNA damage leading to a synergistic, antineoplastic combination with UC41. Agents such as cisplatin, and other DNA alkylating agents may be used.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered intravenously through bolus injections at doses ranging from 25–75 $mg/m^2$ at 21 day intervals for adriamycin, to 35–50 $mg/m^2$ for etoposide intravenously or double the intravenous dose orally.

Agents that disrupt the synthesis and fidelity of nucleic acid precursors and subunits also lead to DNA damage. A number of nucleic acid precursors have been developed for this purpose. Particularly useful are agents that have undergone extensive testing and are readily available, such as 5-fluorouracil (5-FU). Although quite toxic, 5-FU is applicable in a wide range of carriers, including topical. However intravenous administration with doses ranging from 3 to 15 mg/kg/day is commonly used.

Other factors that cause DNA damage and have been used extensively include γ rays, X-rays, and/or the directed delivery of radioisotopes to tumor cells. Other forms of DNA damaging factors also are contemplated such as microwaves and UV-irradiation. It is most likely that all of these factors effect a broad range of damage to DNA, on the precursors of DNA, the replication and repair of DNA, and the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, and in particular to pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the FDA Office of Biologics standards.

The inventors propose that the regional delivery of UC41 antisense constructs to patients with prostate cancer will be a very efficient method for delivering a therapeutically effective gene to counteract the clinical disease. Similarly, chemo- or radiotherapy may be directed to a particular, affected region of the subject's body. Alternatively, systemic delivery of expression construct and/or the agent may be appropriate in certain circumstances, for example, where extensive metastasis has occurred.

In addition to combining UC41-targeted therapies with chemo- and radiotherapies, it also is contemplated that combination with other gene therapies will be advantageous. For example, simultaneous targeting of therapies directed toward UC41 and p53 may produce an improved anti-cancer treatment. Any other tumor-related gene conceivably can be targeted in this manner, for example, p21, Rb, APC, DCC, NF-1, NF-2, p16, FHIT, WT-1, MEN-I, MEN-II, VHL, FCC, MCC, ras, myc, neu, raf erb, src, fins, jun, trk, ret, gsp, hst, bcl and abl.

4.9.4 Screening For Modulators Of UC41

Cells exhibiting elevated UC41 expression may be screened to identify effectors of UC41 expression. Therefore, within certain embodiments of the invention, methods are provided for screening for modulators of UC41 expression. UC41 expression, in turn, may be examined by Northern blot or slot blot analysis of the RNA products of the gene, Western blot analysis of the protein products of the gene, or by other standard techniques as described herein. Compounds which modulate UC41 expression may be detected by their effect on the amounts of these RNA or protein gene products present in a given cell line or tissue sample.

Screening methods may use the target cells as adherent cells on a culture dish, as part of an alginate biomatrix, in suspension culture or in any other form that permits the expression of the polypeptide or nucleic acid to be monitored. These cells are then used as reagents to screen small molecule and peptide libraries to identify modulators of UC41 function.

Regulation of expression can occur at any phase in the synthesis and release of a nucleotide or polypeptide, including gene transcription; stability of the mRNA; translation; post-translational modifications such as proteolytic processing, formation of disulfide bonds, amidation, and glycosylation; and subcellular locallization. Screening methods will monitor the expression of these gene products in the absence of the candidate substance and comparing such results to the assay performed in the presence of candidate substances.

It is contemplated that this screening technique will prove useful in the general identification of a compound that will serve the purpose of decreasing, inhibiting, or otherwise abrogating the expression of UC41. Such compounds will be useful in the treatment of prostate cancer. In these embodiments, the present invention is directed to a method for determining the ability of a candidate substance to inhibit UC41 expression. The method including generally the steps of:

(a) providing at least one UC41 expressing cell;

(b) contacting said cell with said candidate substance;

(c) measuring the level of UC41 expression in said cell; and (d) comparing the UC41 expression of the cell in step (c) with the UC41 expression of the cell of step (a).

To identify a candidate substance as being capable of inhibiting UC41 expression in the assay above, one would measure or determine levels of UC41 expression in an appropriate cell line in the absence of the added candidate substance. One would then add the candidate substance to the cell and determine the level of UC41 expression in the presence of the candidate substance. A candidate substance which decrease UC41 expression relative to the expression level in its absence, is indicative of a candidate regulatory substance for UC41 expression.

As used herein the term "candidate substance" refers to any molecule that is capable of modulating UC41 expression. The candidate substance may be a protein or fragment thereof, a small molecule inhibitor, or even a nucleic acid molecule. It may prove to be the case that the most useful pharmacological compounds for identification through application of the screening assay will be compounds that are structurally related to other known modulators of expression. The active compounds may include fragments or parts of naturally-occurring compounds or may be only found as active combinations of known compounds which are otherwise inactive. However, prior to testing of such compounds in humans or animal models, it will possibly be necessary to test a variety of candidates to determine which have potential.

Accordingly, the active compounds may include fragments or parts of naturally-occurring compounds or may be only found as active combinations of known compounds which are otherwise inactive. Accordingly, the present invention provides screening assays to identify agents which stimulate or inhibit cellular UC41 expression, it is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be polypeptide, polynucleotide, small molecule inhibitors or any other compounds that may be designed through rational drug design starting from known regulators of gene expression, as well as known agents for therapeutic treatment of prostate cancer.

The candidate screening assays are simple to set up and perform. Thus, in assaying for a candidate UC41 regulatory compound, after obtaining a UC41 expressing cell line, one will admix a candidate substance with the cell, under conditions which would allow measurable expression to occur. "Effective amounts" in certain circumstances are those amounts effective to reproducibly stimulate expression from the cell in comparison to their normal levels. Compounds that achieve significant appropriate changes in UC41 expression will be used.

Significant changes in UC41 expression are represented by a decrease in expression of at least about 30% –40%, and most preferably, by decreases of at least about 50%, with higher values of course being possible.

It will, of course, be understood that all the screening methods of the present invention are useful in themselves notwithstanding the fact that effective candidates may not be found. The invention provides methods for screening for such candidates, not solely methods of finding them.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus may be considered to constitute preferred modes for its practice. However, those of skill in the art should, in light of the present disclosure, appreciate that many changes may be made in the particular embodiments which are disclosed and still obtain a like or similar result without departing from the spirit and scope of the invention.

5.1 Materials and Methods 5.1.1 Tissue acquisition

Normal prostate, benign prostatic hyperplasia (BPH), prostate cancer (CaP) and metastatic prostate cancer tissue were from radical prostatectomies. Xenografts were from two cell lines, Lu23 and Lu35, passaged in nude mice. All tissues were either processed immediately for RNA isolation or fresh frozen in liquid nitrogen and then stored at –80° C. for further use. The prostate cancer cell lines LNCaP, PC–3 and DU1145 were maintained in RPMI 1640 medium.

5.1.2 Differential display

A modified Differential Display method (Liang and Pardee, 1992; An et al., 1995) was used to identify UC41 as a gene up-regulated in prostate cancer. Total RNA was isolated from frozen normal prostate and prostate cancer tissues according to Chomczynski and Sacchi (1987). RNA (10 $\mu$g) from each tissue was treated with 5 units of RNase-free DNase I (GIBCO/BRL, Gaithersburg, MD) in the presence of 20 mM Tris-HCl, pH 8.4, 50 mM KCl, 2 mM MgCl$_2$ and 20 units of RNase inhibitor (Boehringer Mannheim Biochemicals, Indianapolis, Ind.). After extraction with phenol/chloroform and ethanol precipitation, the RNA was redissolved in DEPC-treated H$_2$O.

One $\mu$g from each RNA sample was reverse transcribed into cDNA using random hexamers and M-MLV reverse transcriptase (GIBCO/BRL, Gaithersburg, Md.), following the manufacturer's instructions. The reaction mixture contained 50 mM Tris-HCl, pH 8.3, 75 mM KCl, 3 mM MgCl$_2$, 10 mM DTT, 500 μM dNTP, 2 μm random hexamers and 400 U M-MLV reverse transcriptase. PCR™ was performed with two arbitrary 10-mer primers.

Arbitrary primers used for identifying UC41:
5' CTAGTGATTA 3' SEQ ID NO:6
5' GTCCTTATGA 3' SEQ ID NO:7

PCR™ was performed in 1X PCR™ buffer (GIBCO/BRL, Gaithersburg, Md.), 50 μM dNTPs, 0.2 μM arbitrary primer(s), 1/20 volume (1μ) of the cDNA and 1 U of Taq DNA polymerase (GIBCO/BRL, Gaithersburg, Md.) in a final volume of 20 μl. The amplification parameters included 40 cycles of reaction with 30 sec denaturing at 94° C., 1 min 30 sec annealing at 38° C. and 1 min extension at 72° C. A final extension at 72° C. was performed for 15 min. The PCR™ products were then separated on a 3% metaphor agarose gel (FMC BioProducts, Rockland, Me.) with 0.5 μg/ml ethidium bromide and positive bands were identified under UV light. Positive bands were excised with a razor blade, purified on Qiaex resin (Qiagen, Valencia, Calif.) according to the manufacturer's instructions and cloned directly into a plasmid using the TA cloning system (pGEM-T system, Promega, Madison, Wis.). The differential expression of positive bands was confirmed by relative quantitative RT-PCR™.

5.1.3 Prostate cDNA library screening and sequence analysis

An [α-$^{32}$P]-dATP labeled probe was made by random labeling (Gibco/BRL, Gaithersburg, Md.) from a 183 bp EST fragment of UC41 (identified as SEQ ID NO:23 in U.S. patent application Ser. No. 08/692,787 the entire text of which is incorporated herein by reference.) This fragment corresponds to bases 1323–1500 of SEQ ID NO: 1. A normal human prostate cDNA library in λgtll (Clontech) was plated in duplicate and screened according to the product manual. Hybridization of the plated library was performed at 68° C. overnight in ExpressHyb solution (Clontech, Palo Alto, Calif.). Filters were washed twice in 2×SSC, 0.05% SDS at 37° C., then once in 0.1×SSC, 0.1% SDS at 50° C. The labeled filter was exposed to XAR-5 film (Kodak, Rochester, N.Y.) at −70° C.

From about 3×10$^5$ plaques, 2 independent positive clones were isolated after three rounds of screening. The inserts from the two clones were re-amplified and subcloned into sequencing vector pCR2-TOPO (Invitrogen, Carlsbad, Calif.). The sequence was determined by cycle sequencing with both M13 forward and reverse primers and analyzed with Sequencher software (Gene Codes). The complete cDNA sequence identified for UC41 is presented in SEQ ID NO: 1. The full length cDNA fragment (SEQ ID NO: 1) inserted in vector pCR2-TOPO is identified herein as pCR TOPO-UC41. The generated sequence was analyzed for the prediction of open reading frame, translation initiation site, signaling peptide, transmembrane region and potential modification domain.

5.1.4 Northern Blot and Dot Blot Analyses

The probe used to screen Northern blots and dot blots consisted of a 697 bp DNA fragment excised from pCR TOPO-UC41 by Sph I and Pst I digestion and labeled with [α$^{32}$P]-dATP using a random primer DNA labeling kit (Gibco/BRL, Gaithersburg, Md.). The Sph I-Pst I fragment corresponds to bases 157 to 854 of SEQ ID NO: 1. The multiple tissue northern (including eight normal adult tissues) and human RNA master (including 43 adult tissues and 7 fetal tissues) filters (Clontech, Palo Alto, Calif.) containing 2 μg or 89–514 ng, respectively, of normalized poly A$^+$ RNA per lane or dot were hybridized with [α-$^{32}$P]-dATP-labeled probe as described above and exposed to XAR-5 film (Kodak, Rochester, N.Y.) at −70° C. for 3 days.

5.1.5 In situ Hybridization

To generate the probe for in situ hybridization studies, the UC41 cDNA (SEQ ID NO:1) was amplified by PCR™ using the following primers for 30 cycles at 94° C. 30 sec, 58° C. 1 min, 72° C. 1 min each and a final extension of 5 min at 72° C.

Forward primer (at position 1319 of SEQ ID NO:1)
5'-AAAACGATATCATGCTTTCTCATCTCTCC-3' (SEQ ID NO:8)

Reverse primer (at position 1694 of SEQ ID NO:1)
5'-CAATTGCGGCCGCTCTATCAGCCTCTTTGGAG-3' (SEQ ID NO:9)

The PCR™ amplified product was then cloned into the pGEMT-T vector to create the plasmid pGEMT-UC41. Both sense and antisense digoxigenin-dUTP labeled RNA probes were synthesized from 1 μg of linearized plasmid pGEMT-UC41 (digested with Nco I or Eco RV) in a standard in vitro transcription reaction, using the T7 and SP6 promoters and a DIG RNA labeling kit (Boehringer Mannheim, Indianapolis, Ind.).

In situ hybridization was performed with a GenII automatic in situ system (Ventana Medical Systems, Tucson, Ariz.). Sections (5 μm) from formalin-fixed, paraffin-embedded tissue were mounted onto Proma plus slides. The slides were then dewaxed at 65° C. for 2 h and rehydrated. Before hybridization, sections were digested with proteinase I cocktail for 12 min at 37° C. Then 10 ng of either antisense or sense probe in the hybridization buffer, in a volume of 70 μl, were applied to the sections, denatured at 65° C. and then incubated at 42° C. for 360 min. After sequential washing with 2×, 1× and 0.1× SSC buffer, the specific signal was detected using mouse anti-digoxigenin antibody, followed by biotin conjugated anti-mouse antibody and streptavidin-horseradish peroxidase and developed with DAB H$_2$O$_2$.

5.1.6 RT-PCR™

Microdissections of normal prostate and prostate cancer tissues, as guided by hematoxylin and eosin (H&E) staining, were performed on OCT (Optimal Cutting Temperature compound, Miles, Inc., E1 khart IN) embedded tissues taken following radical prostatectomies. Total RNA was isolated from the corresponding normal prostate and prostate cancer tissue, prostate cancer cell lines and xenografts with a STAT 60 kit (Tel-Test, Friendswood, Tex.) according to the manufacturer's instructions. One μg of total RNA from each sample was reverse-transcribed into cDNA with hexamer random primers and a SuperTrancriptase II kit (GIBCO/BRL, Gaithersburg, Md.). One microliter each of the resultant cDNA was amplified by PCR™ for 28 cycles at 94° C. for 30 sec, 58° C. for 1 min, 72° C. for 1 min each, using either the UC41 specific or β$_2$ microglobin primers identified below.

UC41 forward primer (position 169 of SEQ ID NO:1)
5'-CAAATAGCAAGCCCTGCCCACTCA-3' (SEQ ID NO:10)

UC41 reverse primer (position 503 of SEQ ID NO:1)
5'-CTCCTAATCTCACCCCTTCCGCTAT-3' (SEQ ID NO:11)

β$_2$ microglobin forward primer
5'-CACGTCATCCAGCAGAGAATGGAAAGTC-3' (SEQ ID NO: 12)

β$_2$ microglobin reverse primer
5'-GAGAATAGGTTGTAGTTGTAGAACCAGT-3' (SEQ ID NO:13)

5.1.7 Chromosomal Locallization of the UC41 Gene by FISH

The chromosomal location of UC41 was identified by FISH using the procedure of Heng et al. (1992). Lymphocytes isolated from human blood were cultured in minimum essential medium (MEM) supplemented with 10% fetal calf serum and phytohemagglutinin (PHA) at 37° C. for 68–72 h. The lymphocyte cultures were then treated with bromodeoxyuridine (BrdU, 0.18 mg/ml, Sigma Chemical Co., St. Louis, Mo.) to synchronize the cell population. The cells were washed with serum-free medium to release the block in cell cycle and recultured at 37° C. for 6 h in MEM with thymidine (2.5 µg/ml, Sigma).

Cells were harvested and slides were made by standard procedures, including hypotonic treatment and fixation followed by air-drying. Slides were baked at 55° C. for 1 h. After treatment with RNase, the slides were denatured in 70% formamide in 2× SSC for 2 min at 70° C., followed by ethanol dehydration. A 0.9 kb UC41 cDNA probe was biotinylated with dATP for 1 h at 15° C. using a BioNick labeling kit (GIBCO/BRL, Gaithersburg, Md.). The probe was prepared by Hpa I and Nco I digestion and corresponds to bases 870 to 1840 of SEQ ID NO: 1.

The labeled probe was denatured at 75° C. for 5 min in a hybridization solution containing 50% formamide, 10% dextran sulfate and human Cot I DNA. The denatured probe was added to the slides and allowed to hybridize with chromosomal DNA overnight. Slides were then washed, detected and amplified by standard procedures. FISH signals and DAPI banding pattern were recorded separately by sequential photography of the same microscope field. The assignment of the FISH mapping data with chromosomal bands was achieved by superimposing FISH signals on the DAPI banded chromosomes.

A Stanford G3 panel (Research Genetics, Huntsville, Ala.) was used to determine the linkage of UC41 with known microsatellite markers. The G3 panel contained 83 hamster-human radiation-reduced cell hybrids with an estimated resolution of approximately 500 kb. PCR™ was performed with the following UC41 specific primers.

Forward primer (at position 1191 of SEQ ID NO:1)

5'-CTGCCAACTTCCTCTCTATGC-3'(SEQ ID NO:14)

Reverse primer (at position 1707 of SEQ ID NO:1)

5'-GTCCTCATCTATCAGCCTCTTTG-3' (SEQ ID NO:15)

Thermal cycling was performed for 35 cycles at 94° C. for 30 sec, 56° C. for 1 min, 72° C. for 1 min, followed by extension at 72° C. for 10 min. The PCR™ product was resolved in 1% agarose gel and the G3 panel of UC41 was ordered using the RII-MAP program on the RH server (University of Washington).

Example 1

Figure 1B:
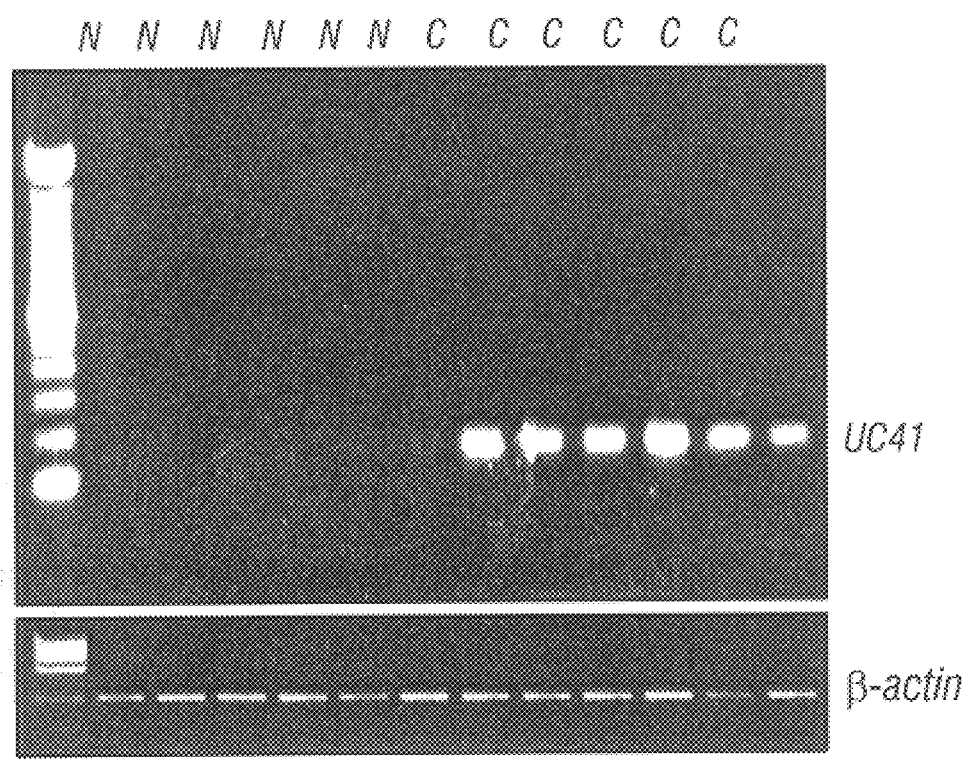

Identification of UC41 as an Overexpressed Gene in Prostate Cancer by Differential Display A modified agarose gel-based mRNA differential display method was used to identify genes differentially expressed in prostate cancer tissue. UC41 was identified as a gene that was very significantly up-regulated in prostate cancer. As shown in FIG. 1 (panel A), a strong band (UC41) was seen in all three prostate cancer tissues used for the differential display study, while UC41 band intensity was very low all four normal tissues tested.

The UC41 band was excised, purified and cloned directly into the pGEM-T plasmid by TA cloning. The UC41 cDNA clone was sequenced by standard techniques as described above. The resulting 183 bp EST fragment of UC41 (identified as SEQ ID NO:23 in U.S. patent application Ser. No. 08/692,787 the entire text of which is incorporated herein by reference) corresponds to bases 1323–1500 of SEQ ID NO:1.

Using this sequence data, forward and reverse primers for UC41 (SEQ ID NO:10 and SEQ ID NO:11) were designed and used in a relative quantitative RT-PCR™ study, as described above, to confirm the up-regulation of this gene in prostate cancer. As shown in FIG. 1, panel B, the expression of UC41 was confirmed to be significantly up-regulated in all six prostate cancer tissues tested, while expression was very low in normal prostate tissues. Separate studies confirmed that expression of UC41 is significantly elevated in prostate cancer compared with BPH. Thus, overexpression of UC41 appears to be diagnostic for malignant prostate tumors.

Figure 2:
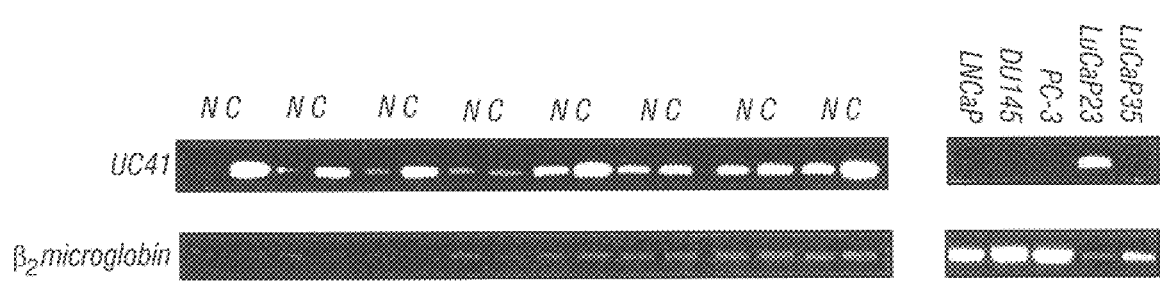
FIG. 2. (Scanned image) UC41 expression in pair-matched normal and cancer tissues. The pair-matched tissue was microdissected from OCT embedded radical prostatectomies as described below in the section MATERIAL AND METHODS. $\beta_2$ microglobin RT-PCR™ was used as a control. Matched samples were from normal prostate (N) and adjacent prostate cancer tissues (C). The insert on the far right side of the FIG. shows the results of RT-PCR™ for UC41 and $\beta_2$ microglobin in the LNCaP, PC-3 and DU145 prostate cancer cell lines and the Lu 23 and Lu 35 prostate cancer xenografts.

The expression of UC41 was compared in pair-matched samples of normal prostate and prostate cancer tissues taken from the same subjects, as determined by semi-quantitative RT-PCR™. All eight samples show increased expression of UC41 in prostate cancer tissues, with different degrees of overexpression observed in individual subjects (FIG. 2). UC41 expression was examined in three prostate cancer cell lines, LNCaP, PC-3, DU145 and two CaP xenografts, Lu 23 and Lu 35. Lu 23 expressed a high level of UC41, while Lu 35 showed relatively low expression and the three prostate cancer cell lines were almost negative for expression of UC41 (FIG. 2).

Example 2

Isolation of a Full Length cDNA Clone of UC41

The 183 bp UC41 fragment identified in Example 1 was used as a probe to screen a normal prostate tissue cDNA library. This screen yielded six independent positive clones on duplicated filters (containing over 3×10$^6$ recombinant clones). These six isolated clones were subjected to further screening. Two of these clones gave strong positive signals on repetitive hybridization. The inserts of these two clones were amplified with flanking M13 primers and subcloned into the Top vector (Invitrogen, Carlsbad, Calif.). DNA sequences were determined from the both ends of the inserts and found to overlap with each other and with the UC41 fragment identified by differential display.

The full-length cDNA for UC41 gene was cloned by a combination of cDNA library screening and RACE (Rapid Cloning of cDNA Ends) methods (Frohman, 1990 incorporated by reference). The complete, 1934 bp cDNA sequence identified is shown in SEQ ID NO:1 (FIG. 9).

Bioinformatic-generated translation analysis of the cDNA indicated an ORF (open reading frame) of 125 amino acids (SEQ ID NO:2), with an ATG initiation codon at bp 1320 of SEQ ID NO:1 and a termination codon at bp 1695 of SEQ ID NO:1. The 183 bp EST identified in Example 1 starts immediately after the initiation codon and ends approximately halfway through the ORF.

The translated protein has a calculated molecular mass of 13.7 kDa and an isoelectric pH of 10.48. Two potential myristylation sites are located at residues 59–64 (GQVSTR) and 80–85 (GISNSG) of SEQ ID NO:2. Three putative protein kinase C phosphorylation sites are located at residues 27–29 (TLR), 62–64 (STR) and 84–86 (SGR) of SEQ ID NO:2. A hydropathy plot of SEQ ID NO:2 yielded a lightly hydrophilic N-terminal region that may serve as a signal peptide (residues 2–24 of SEQ ID NO:2) and a strongly hydrophobic C-terminal area which has the characteristic of a transmembrane domain (residues 99–121 of SEQ ID NO:2). Extensive computer homology searches conducted in the GenBank, ECM, and Swiss sequence banks did not find any known nucleotide/amino acid sequence having homology with the UC41 cDNA or deduced amino acid sequences.

Example 3

In Situ Hybridization

Figure 3:
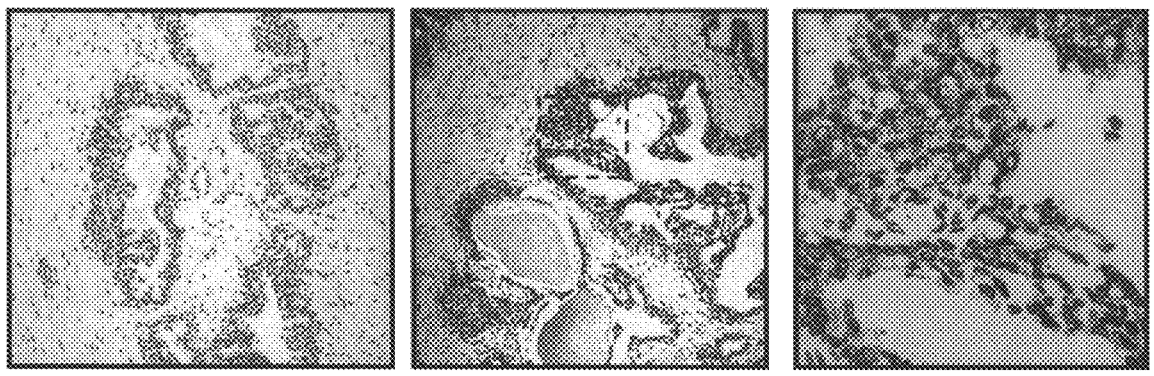
FIG. 3. In situ hybridization performed with both sense and antisense probes labeled with digoxigenin-dUTP as described below in the section MATERIAL AND METHODS. UC41 was predominantly expressed in the basal cells of normal prostate (far left). Its expression was upregulated in prostate cancer (middle and far right).
Figure 4:
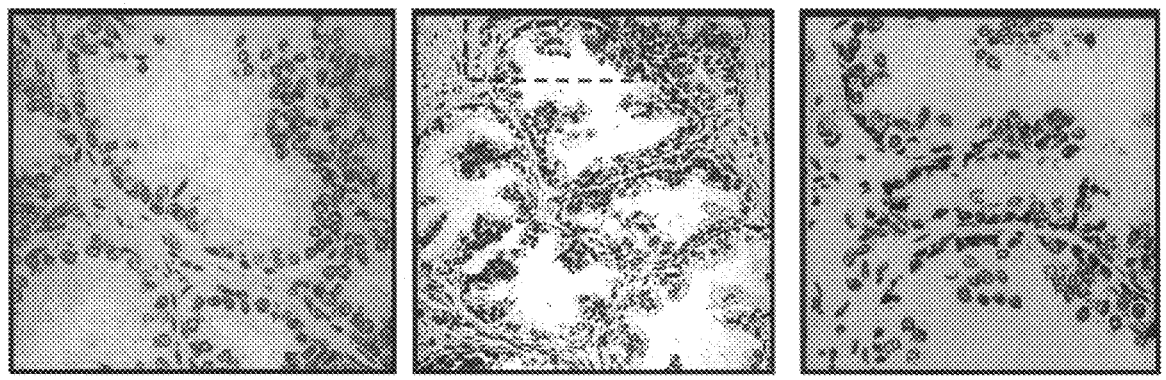
FIG. 4. In situ hybridization performed with both sense and antisense probes labeled with digoxigenin-dUTP as described below in the section MATERIAL AND METHODS. UC41 was predominantly expressed in the basal cells of normal prostate (far left). Its expression was upregulated in prostate cancer metastatic to lymph nodes (middle and far right).
Figure 5:
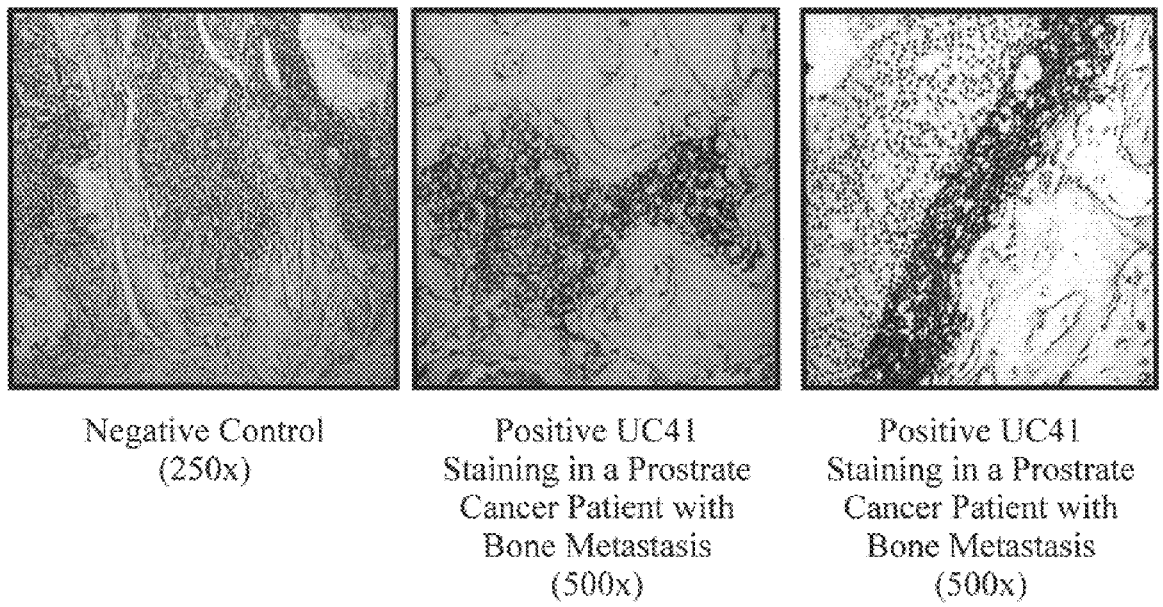
FIG. 5. In situ hybridization performed with both sense and antisense probes labeled with digoxigenin-dUTP as described below in the section MATERIAL AND METHODS. UC41 was predominantly expressed in the basal cells of normal prostate (far left). Its expression was upregulated in prostate cancer metastatic to bone (middle and far right).

Studies were performed to investigate the expression of UC41 and to localize UC41 mRNA in formalin-fixed paraffin-embedded prostate cancer and prostate cancer metastatic to lymph node and bone, compared with normal prostate tissue. FIG. 3 shows a comparison of UC41 staining in prostate cancer tissue compared to normal prostate. A significant level of UC41 was localized in prostate adenocarcinoma tissue, while only minimal levels of UC41 mRNA were detected in adjacent samples of normal and benign prostatic epithelial cells (FIG. 3). UC41 expression in normal prostate tissue appears to be locallized to luminal epithelial cells, preferentially in luminal basal cells. (FIG. 3) Prostate cancer cells metastatic to the lymph nodes showed very heavy staining with a UC41 mRNA probe (FIG. 4), while normal lymph nodes exhibited no detectable staining (FIG. 4). Similar results were observed with metastatic prostate cancer cells in bone marrow, compared to normal bone marrow (FIG. 5).

Example 4

Specific Expression of UC41 in Prostate Tissue

Figure 6:
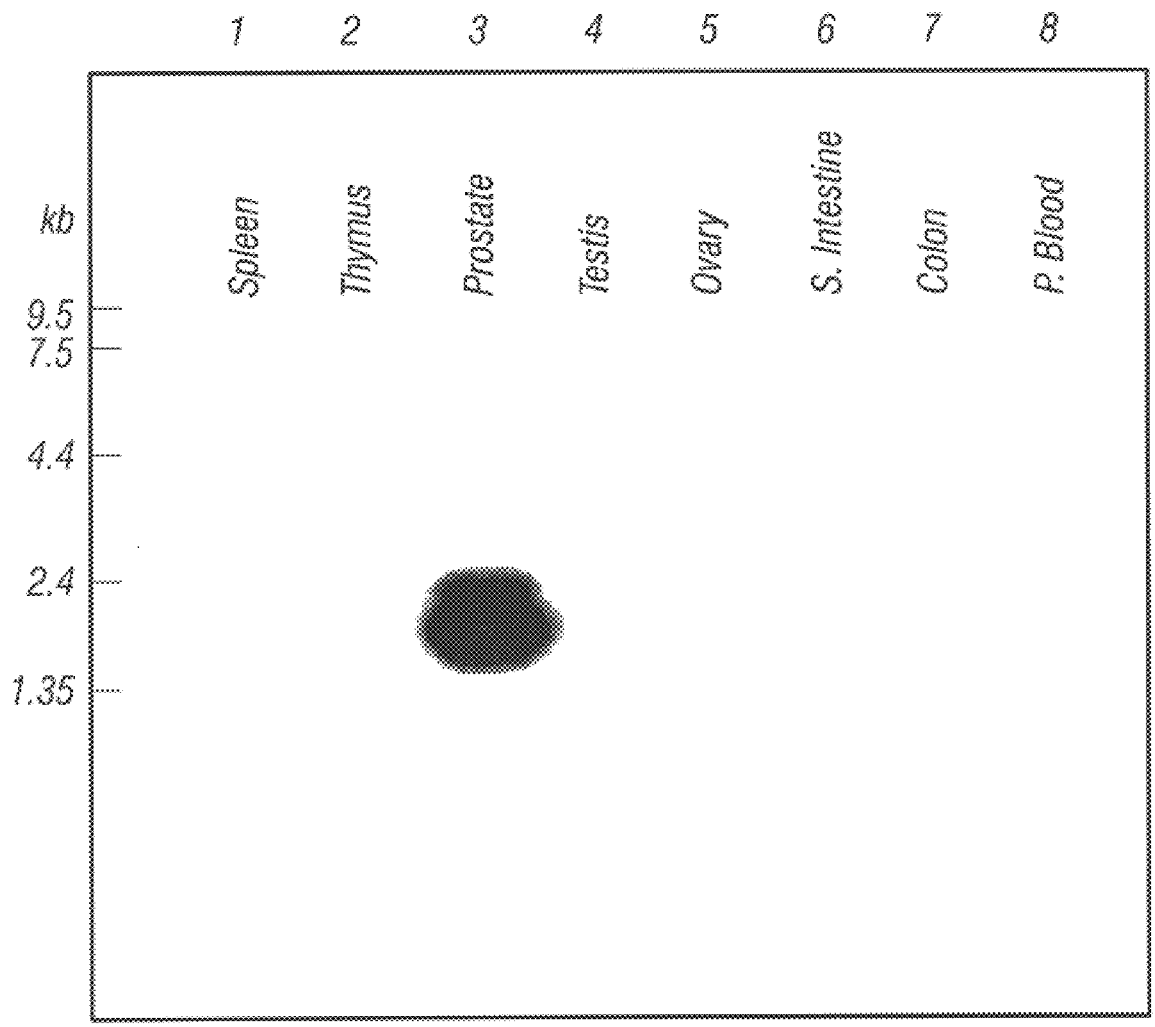
FIG. 6. (Scanned image) Expression of UC41 in different normal tissues analyzed by Northern blot hybridization. The human multiple tissue northern blot (Clontech, 2 µg of poly A⁺ RNA per lane) was blotted as described below in the section MATERIAL AND METHODS. Relative expression of UC41 is shown in human spleen (lane 1), thymus (lane 2), prostate (lane 3), testis (lane 4), ovary (lane 5), small intestine (lane 6), colon (mucosal lining, lane 7) and peripheral blood leukocyte tissues (lane 8). The UC41 band of approximately 2.4 kb is expressed only in normal prostate tissue.

Tissue-specific expression of UC41 was examined by Northern blot analysis with with mRNA from spleen, thymus, prostate, testis, ovary, small intestine, colon and peripheral blood leukocytes (FIG. 6). A strong hybridization signal was observed specifically in prostate tissue (FIG. 6). The results in prostate are consistent with the existence of two different splicing variants of the UC41 gene, with a major band migrating at approximately 1.5 kb and a minor band at approximately 2.1 kb (FIG. 6). These results indicated that expression of the UC41 gene is specific for prostate tissue.

The prostate specific expression of UC41 was confirmed by dot blot hybridization, using an expanded panel of RNA samples from fifty different adult human or fetal human tissues (FIG. 7). A strong hybridization signal was again observed only in prostate RNA (FIG. 7), with a very minor amount of hybridization detected in bladder RNA (FIG. 7).

Example 5

Chromosomal Localization of UC41

The chromosomal locus of UC41 was identified by comparison of UC41 FISH hybridization (FIG. 8, panel A) and DAPI staining (FIG. 8, panel B). Based on this comparison, UC41 was assigned to the long arm of chromosome 3. The detailed position of UC41 was further determined based on a summary of data from 10 different FISH/DAPI comparisons (FIG. 8, insert on far right), which mapped the gene to 3q22–23. Both FISH mapping (FIG. 8) and human genomic DNA Southern hybridization indicate that the UC41 gene exists as a single copy.

UC41 was typed on the G3 radiation hybrid panel developed at Stanford and analyzed with the RH-MAP program (University of Washington), as described above. The two-point analyses ordered UC41 with the microsatellite marker D3S1541, with a distance of 11 cR (about 250 kb).

Those experienced in the art will recognize that the gene and gene products (RNAs and proteins) for UC41 are included within the scope of the invention herein described. Those experienced in the art will also recognize that the diagnosis and prognosis of prostatic cancer by detection of the nucleic acid or protein products of this gene are included within the scope of the present invention.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following literature citations as well as those cited above are incorporated in pertinent part by reference herein for the reasons cited in the above text.

Alcaraz et al., *Cancer Res.*, 55:3998–4002, 1994.
Allhoff et al., *World J. Urol.*, 7:12–16, 1989.
An et al., *Proc. Amer. Assn. Canc. Res.*, 36:82, 1995.
An et al., *Molec. Urol.*, 2: 305–309, 1998.
Antibodies: A Laboratory Manual., Cold Spring Harbor Laboratory, Cold Spring Harbor Press, Cold Spring Harbor, N.Y., 1988.
Babian et al., *J. Urol.*, 156:432–437, 1996.
Badalamentet al., *J. Urol.*, 156: 1375–1380, 1996.
Baichwal and Sugden, In: *Gene Transfer*, Kucherlapati (Ed.), Plenum Press, New York, pp 117–148, 1986.
Banghametal., *J. Mol. Biol.* 13: 238–252, 1965.
Barinaga, *Science,* 271: 1233, 1996.
Bedzyk et al., *J. Biol. Chem.,* 265:18615, 1990
Bell et al., "Gynecological and Genitourinary Tumors," In: *Diagnostic Immunopathology*, Colvin, Bhan and McCluskey (Eds.), 2nd edition, Ch. 31, Raven Press, New York, pp 579–597, 1995.
Bellus, *J. Macromol. Sci. Pure Appl. Chem.,* A31(1): 1355–1376, 1994.
Benvenisty and Neshif, *Proc. Nat. Acad. Sci. USA,* 83:9551–9555, 1986.
Bittner et al., *Methods in Enzymol.,* 153:516–544, 1987.
Bookstein et al., *Science,* 247:712–715, 1990a.
Bookstein et al., *Proc. Nat'l Acad. Sci. USA,* 87:7762–7767, 1990b.
Bovaet al., *Cancer Res.,* 53:3869–3873, 1993.
Brawn et al., *The Prostate,* 28: 295–299, 1996.
Campbell, In: *Monoclonal Antibody Technology, Laboratory Techniques in Biochemistry and Molecular Biology*, Burden and Von Knippenberg (Eds.), Vol. 13:75–83, Elsevier, Amsterdam, 1984.
Capaldi et al., *Biochem. Biophys. Res. Comm.,* 76:425, 1977.
Carter and Coffey, In: Prostate Cancer. The Second Tokyo Symposium, J. P. Karr and H. Yamanak (Eds.), Elsevier, N.Y., pp 19–27, 1989.
Carter and Coffey, Prostate, 16:39–48, 1990.
Carter et al., *Proc. Nat'l Acad. Sci. USA,* 87:8751–8755, 1990.

Carter et al., *Proc. Nat'l Acad. Sci. USA* 93: 749–753, 1996.
Carter et al., *J. Urol.,* 157:2206–2209, 1997.
Cech et al., *Cell,* 27:487–496, 1981.
Chang et al., *Hepatology,* 14:124A, 1991.
Chaudhary et al., *Proc. Nat'l Acad. Sci.,* 87:9491, 1990
Chen and Okayama, *Mol. Cell Biol,* 7:2745–2752, 1987.
Chen et al., *Clin. Chem.,* 41:273–282, 1995a.
Chen et al., *Proc. Am. Urol. Assn.,* 153:267A, 1995.
Chinault and Carbon, "Overlap Hybridization Screening: Isolation and Characterization of Overlapping DNA Fragments Surrounding the LEU2 Gene on Yeast Chromosome III," *Gene,* 5:111–126, 1979.
Chomczynski and Sacchi, *Anal. Biochem.,* 162:156–159, 1987.
Christensson et al., *J. Urol.,* 150:100–105, 1993.
Coffin, In: *Virology,* Fields et al. (Eds.), Raven Press, New York, pp 1437–1500, 1990.
Colberre-Garapinet al., *J. Mol. Biol.,* 150:1, 1981.
Colvin et al., *Diagnostic Immunopathology,* 2nd edition, Raven Press, New York, 1995.
Cooner et al., *J. Urol.,* 143:1146–1154, 1990.
Couch et al., *Am. Rev. Resp. Dis.,* 88:394–403, 1963.
Coupar et al., *Gene,* 68:1–10, 1988.
Culver et al., *Science,* 256:1550–1552, 1992.
Davey et al., EPO No.329 822.
Deamer and Uster, "Liposome Preparation: Methods and Mechanisms," In: *Liposomes,* M. Ostro (Ed.), 1983.
Diamond et al., *J. Urol.,* 128: 729–734, 1982.
Donahue et al., *J. Biol. Chem.,* 269:8604–8609, 1994.
Dong et al., *Science,* 268:884–886, 1995.
Dubensky et al., *Proc. Nat. Acad. Sci. USA,* 81:7529–7533, 1984.
Dumont et al., *J. Immunol.,* 152:992–1003, 1994.
Elledge et al., *Cancer Res.* 54:3752–3757, 1994
European Patent Application EPO No. 320 308
Fearon et al., *Science,* 247:47–56, 1990.
Fechheimer et al., *Proc. Natl. Acad. Sci. USA,* 84:8463–8467, 1987.
Forster and Symons, *Cell,* 49:211–220, 1987.
Fraley et al., *Proc. Natl. Acad. Sci. USA,* 76:3348–3352, 1979.
Friedmann, *Science,* 244:1275–1281, 1989.
Freifelder, In: *Physical Biochemistry Applications to Biochemistry and Molecular Biology,* 2nd ed., Wm. Freeman and Co., New York, N.Y., 1982.
Frohman, In: *PCR Protocols: A Guide to Methods and Applications,* Academic Press, New York, 1990.
Gefter et al., *Somatic Cell Genet.,* 3:231–236, 1977.
Gerlach et al., *Nature* (London), 328:802–805, 1987.
Ghosh-Choudhury et al., *EMBO J.,* 6:1733–1739, 1987.
Gingeras et al., PCT Application WO 88/10315.
Ghosh and Bachhawat, In: *Liver Diseases, Targeted Diagnosis and Therapy Using Specific Receptors and Ligands,* Wu et al. (Eds.), Marcel Dekker, New York, pp 87–104, 1991.
Goding,In: *Monoclonal Antibodies:Principles and Practice,* 2d ed., Academic Press, Orlando, Fla., pp 60–61, 65–66, 71–74, 1986.
Gomez-Foix et al., *J. Biol. Chem.,* 267:25129–25134, 1992.
Gopal., *Mol. Cell Biol.,* 5:1188–1190, 1985.
Graham et al., *J. Gen. Virol.,* 36:59–72, 1977.
Graham and van der Eb, *Virology,* 52:456–467, 1973.
Graham and Prevec, In. *Methods in Molecular Biology: Gene Transfer and Expression Protocols* 7, E. J. Murray (Ed.), Humana Press, Clifton, N.J., pp 205–225. 1991.
Gregoriadis (ed.), In: *Drug Carriers in Biology and Medicine,* pp 287–341, 1979.
Grunhaus and Horwitz, *Sem. Virol.,* 3:237–252, 1992.
Harland and Weintraub, *J. Cell Biol.,* 101: 1094–1099, 1985.
Harris etal., *J. Urol.,* 157:1740–1743, 1997.
Heng et al., *Proc. Nat. Acad. Sci. USA,* 89: 9509–9513, 1992.
Hermonat and Muzycska, *Proc. Nat. Acad. Sci. USA,* 81:6466–6470, 1984.
Hersdorffer et al., DNA Cell Biol., 9:713–723, 1990.
Herz and Gerard, *Proc. Natl Acad. Sci. USA,* 90:2812–2816, 1993.
Hess et al., *J. Adv. Enzyme Reg.,* 7:149, 1968.
Hitzeman et al., *J. Biol. Chem.,* 255:2073, 1980.
Holland et al., *Biochemistry,* 17:4900, 1978.
Horoszewicz, Kawinski and Murphy, *Anticancer Res.,* 7:927–936, 1987.
Horwich, et al., *J. Virol.,* 64:642–650, 1990.
Huang et al., *Prostate,* 23: 201–212, 1993.
Innis et al., In: *PCR Protocols,* Academic Press, Inc., San Diego Calif., 1990 .
Inouye et al., *Nucl. Acids Res.,* 13:3101–3109, 1985.
Isaacs et al., *Cancer Res.,* 51:4716–4720, 1991.
Isaacs et al., *Sem. Oncol.,* 21:1–18, 1994.
Israeli et al., *Cancer Res.,* 54:1807–1811, 1994.
Jacobson et al., *JAMA,* 274:1445–1449, 1995.
Johnson et al., In: *Biotechnology and Pharmacy,* Pezzuto et al., (Eds.), Chapman and Hall, New York, 1993.
Jones, *Genetics,* 85:12, 1977.
Jones and Shenk, *Cell,* 13:181–188, 1978.
Joyce, *Nature,* 338:217–244, 1989.
Kanedaet al., *Science,* 243:375–378, 1989.
Kato et al., *J. Biol. Chem.,* 266:3361–3364, 1991.
Kim and Cech, *Proc. Natl. Acad. Sci. USA,* 84:8788–8792, 1987.
Kingsman et al., *Gene,* 7:141, 1979.
Klein et al., *Nature,* 327:70–73, 1987.
Kohler and Milstein, *Nature,* 256:495–497, 1975.
Kohler and Milstein, *Eur. J. Immunol.,* 6:511–519, 1976.
Kwoh et al., *Proc. Nat. Acad. Sci. USA,* 86:1173, 1989.
Landis et al., *CA Cancer J. Clin.,* 48: 6–29, 1998.
Le Gal La Salle et al., *Science,* 259:988–990, 1993.
Levrero et al., *Gene,* 101:195–202, 1991.
Liang and Pardee, *Science,* 257:967–971, 1992.
Liang and Pardee, U.S. Pat. No. 5,262,311, 1993.
Liang et al., *Cancer Res.,* 52:6966–6968, 1992.
Lifton, *Science,* 272:676, 1996.
Lilja et al., *Clin. Chem.,* 37:1618–1625, 1991.
Lithrup et al., *Cancer,* 74:3146–3150, 1994.
Lowy et al., i Cell, 22:817, 1980.
Macoskaet al., *Cancer Res.,* 54:3824–3830, 1994.
Mann et al., *Cell,* 33:153–159, 1983.
Markowitz et al., *J. Virol.,* 62:1120–1124, 1988.
Marley et al., *Urology,* 48(6A): 16–22, 1996.
McCormack et al., *Urology,* 45:729–744, 1995.
Michel and Westhof, *J. Mol. Biol.* 216:585–610, 1990.
Miki et al., *Science,* 266:66–71, 1994.
Miller et al., PCT Application, WO 89/06700.
Moketal., *Gynecol. Oncol.,* 52:247–252, 1994.
Morahan et al., *Science* 272:1811, 1996.
Mulligan et al., *Proc. Nat'l Acad. Sci. USA,* 78:2072, 1981.
Mulligan, *Science,* 260:926–932, 1993.
Murphy et al., *Cancer,* 78: 809–818, 1996.
Murphy et al., *Prostate,* 26:164–168, 1995.
Nakamuraet al., In. *Handbook of Experimental Immunology,* (4th Ed.), Weir, E., Herzenberg, L. A., Blackwell, C., Herzenberg, L. (Eds.), Vol. 1, Chapter 27, Blackwell Scientific Publ., Oxford, 1987.
Nicolas and Rubinstein, In. Vectors. *A Survey of Molecular Cloning Vectors and Their Uses,* Rodriguez and Denhardt (Eds.), Butterworth, Stoneham, pp 494–513, 1988.

Nicolau and Sene, *Biochim. Biophys. Acta,* 721:185–190, 1982.
O'Dowdetal., *J. Urol.,* 158:687–698, 1997.
O'Hare et al., *Proc. Nat'l Acad. Sci. USA,* 78:1527, 1981.
Oesterling et al., *J. Urol.,* 154:1090–1095, 1995.
Ohara et al., *Proc. Nat'l Acad. Sci. USA,* 86:5673–5677, 1989.
Orozco et al., *Urology,* 51:186–195, 1998.
Parker et al., *CA Cancer J. Clin.,* 65:5–27, 1996.
Partin and Oesterling, *Urology,* 48 (6A): 1–3, 1996.
Partin and Oesterling, *J. Urol.,* 152:1358–1368, 1994.
Partin and Oesterling (Eds.), *Urology,* 48(6A) Supplement: 1–87, 1996.
Paskind et al., *Virology,* 67:242–248, 1975.
PCT Application No. PCT/US87/00880
Pettersson et al., *Clin. Chem.,* 41(10):1480–1488, 1995.
Piironen et al., *Clin. Chem.* 42:1034–1041, 1996.
Potter et al., *Proc. Nat. Acad. Sci. USA,* 81:7161–7165, 1984.
Racher et al., *Biotechnology Techniques,* 9:169–174, 1995.
Ragot et al., *Nature,* 361:647–650, 1993.
Ralph and Veltri, *Advanced Laboratory,* 6:51–56, 1997.
Ralph et al., *Proc. Natl. Acad. Sci. USA,* 90(22): 10710–10714, 1993.
Reinhold-Hurek and Shub, *Nature,* 357:173–176, 1992.
Renan, *Radiother. Oncol.,* 19:197–218, 1990.
Ribas de Pouplana and Fothergill-Gilmore,*Biochemistry,* 33:7047–7055, 1994.
Rich et al., *Hum. Gene Ther.,* 4:461–476, 1993.
Ridgeway, In: *Vectors: A Survey of Molecular Cloning Vectors and Their Uses,* Rodriguez R L, Denhardt DT (Eds.), Butterworth, Stoneham, pp 467–492, 1988.
Rippe et al., *Mol. Cell Biol.,* 10:689–695, 1990.
Rosenfeld et al., *Science,* 252:431–434, 1991.
Rosenfeld et al., *Cell,* 68:143–155, 1992.
Roux et al., *Proc. Nat'l Acad. Sci. USA,* 86:9079–49083, 1989.
Sager et al., *FASEB J.,* 7:964–970, 1993.
Sambrook et al., (ed.), In: *Molecular Cloning,* Cold Spring Harbor Laboratory Press, Cold Spring Harbor, N.Y., 1989.
Santerre et al., *Gene,* 30: 147–156, 1984.
Sarver, et al., *Science,* 247:1222–1225, 1990.
Scanlon et al., *Proc Nat'l Acad Sci USA,* 88:10591–10595, 1991.
Sidransky et al., *Science,* 252:706–709, 1991.
Sidransky et al., *Cancer Res.,* 52:2984–2986, 1992.
Silveretal., *Clin. Cancer Res.,* 3:81–85, 1997.
Slamon et al., *Science,* 224:256–262, 1984.
Slamon et al., *Science,* 235:177–182, 1987.
Slamon et al., *Science,* 244:707–712, 1989.
Smith, U.S. Pat. No. 4,215,051.
Soh et al., *J. Urol.,* 157:2212–2218, 1997.
Stenman et al., *Cancer Res.,* 51:222–226, 1991.
Stinchcomb et al., *Nature,* 282:39, 1979.
Stratford-Perricaudetand Perricaudet, In: *Human Gene Transfer,* O. Cohen-Haguenauer et al., (Eds.), John Libbey Eurotext, France, pp 51–61, 1991.
Stratford-Perricaudet et al., *Hum. Gene. Ther.,* 1:241–256, 1990.
Sun and Cohen, *Gene,* 137:127–132, 1993.
Szoka and Papahadjopoulos,*Proc. Natl. Acad. Sci. USA,* 75: 4194–4198, 1978.
Szybalska et al.,*Proc. Nat'l Acad. Sci. USA,* 48:2026, 1962.
Takahashi et al., *Cancer Res.,* 54:3574–3579, 1994.
Taparowsky et al., *Nature,* 300:762–764, 1982.
Temin, In: *Gene Transfer,* Kucherlapati R. (Ed.), Plenum Press, New York, pp 149–188, 1986.
Tooze, In: *Molecular Biology of DNA Tumor Viruses,* 2nd ed., Cold Spring Harbor Laboratory, Cold Spring Harbor, N.Y., 1991.
Top et al., *J. Infect. Dis.,* 124:155–160, 1971.
Tschemper et al., *Gene,* 10:157, 1980.
Tur-Kaspa et al., *Mol. Cell Biol.,* 6:716–718, 1986.
U.S. patent application Ser. No. 08/692,787
U.S. Pat. No. 4,196,265
U.S. Pat. No. 4,215,051
U.S. Pat. No. 4,683,195
U.S. Pat. No. 4,683,202
U.S. Pat. No. 4,800,159
U.S. Pat. No. 4,883,750
U.S. Pat. No. 5,354,855
U.S. Pat. No. 5,359,046
Varmus et al., *Cell,* 25:23–36, 1981.
Veltri et al., *J. Cell Biochem.,* 19(suppl):249–258, 1994.
Veltri et al., *Urology,* 48: 685–691, 1996.
Veltrietal., *Sem. Urol. Oncol.,* 16:106–117, 1998.
Veltri et al., *Urology,* 53:139–147, 1999.
Visakorpi et al., *Am. J. Pathol.,* 145:1–7, 1994.
Wagner et al., *Science,* 260:1510–1513, 1993.
Walker et al.,*Proc. Nat'l Acad. Sci. USA,* 89:392–396,1992.
Watson et al., *Cancer Res.,* 54:4598–4602, 1994.
Welsh et al., *Nucl. Acids Res.,* 20:4965–4970, 1992.
Wigler et al., *Cell,* 11:223, 1977.
Wigler et al., *Proc. Nat'l Acad. Sci. USA,* 77:3567, 1980.
Wingo et al., *CA Cancer J Clin.,* 47: 239–242, 1997.
WO 90/07641, filed Dec. 21, 1990.
Wong et al., *Int. J. Oncol.,* 3:13–17, 1993.
Wu and Wu, *J. Biol. Chem.,* 262: 4429–4432, 1987.
Wu and Wu, *Biochemistry,* 27: 887–892, 1988.
Wu and Wu,*Adv. Drug Delivery Rev.,* 12: 159–167, 1993.
Wu et al., *Genomics,* 4:560, 1989.
Yang et al., *Proc. Natl. Acad. Sci. USA,* 87:9568–9572, 1990.
Yokoda et al., *Cancer Res.* 52, 3402–3408, 1992.
Zlotta etal., *J. Urol.,* 157:1315–1321, 1997.

What is claimed is:

1. An isolated nucleic acid segment comprising a full length sequence or the full length complement of a sequence selected from the group consisting of SEQ ID NO:1, SEQ ID NO:3 SEQ ID NO:4.

2. An isolated nucleic acid molecule of a size between about 14 and 100 bases in length, identical in sequence to a contiguous portion of at least 14 bases of a nucleic acid or its complement selected from the group consisting of SEQ ID NO:3 and SEQ ID NO:4.

3. The isolated nucleic acid molecule of claim 2, of a size of between about 17 and 100 bases in length.

4. The isolated nucleic acid molecule of claim 2, of a size of between about 20 and 100 bases in length.

5. The isolated nucleic acid molecule of claim 2, of a size of between about 25 and 100 bases in length.

6. The isolated nucleic acid molecule of claim 2, of a size of between about 30 and 100 bases in length.

7. The isolated nucleic acid according to claim 1, wherein the sequence is SEQ ID NO:1.

8. The isolated nucleic acid according to claim 1, wherein the sequence is SEQ ID NO:3.

9. The isolated nucleic acid according to claim 1, wherein the sequence is SEQ ID NO:4.

10. An isolated nucleic acid encoding a full length amino acid sequence selected from the group consisting of SEQ ID NO:2 and SEQ ID NO:5.

11. A prostate cancer detecting kit, comprising:
(a) a primer pair for amplifying a nucleic acid comprising a sequence selected from the group consisting of SEQ ID NO:3 and SEQ ID NO:4 wherein said oligonucleotide probes are at least 14 bases in length; and
(b) containers for each of said primers.

12. A kit for use in detecting prostate cancer cells in a biological sample, comprising:
(a) an oligonucleotide probe which binds under high stringency conditions to an isolated nucleic acid comprising a sequence selected from the group consisting of SEQ ID NO:3 and SEQ ID NO:4; and
(b) a container for said probe.

13. The isolated nucleic acid according to claim 1, wherein said nucleic acid is incorporated into a human expression vector.

14. The isolated nucleic acid according to claim 10, wherein said nucleic acid is incorporated into a human expression vector.

* * * * *

UNITED STATES PATENT AND TRADEMARK OFFICE
CERTIFICATE OF CORRECTION

PATENT NO. : 6,156,515  
DATED : December 5, 2000  
INVENTOR(S) : Gang An and Robert Veltri Page 1 of 1

It is certified that error appears in the above-identified patent and that said Letters Patent is hereby corrected as shown below:

Column 73,  
Line 59, after "SEQ ID NO:3" insert -- and --.

Column 75,  
Line 7, after "said", delete "oligonucleotide probes" and insert -- primers -- therefor.  
Line 10, after "A", insert -- prostate cancer detecting -- and after "kit" delete "for use in detecting prostate cancer cells in a biological sample".

Column 76,  
Line 2, after "SEQ ID NO:4", insert -- wherein said oligonucleotide probes are at least 14 bases in length --.

Signed and Sealed this

Seventh Day of May, 2002

Attest:

Attesting Officer

JAMES E. ROGAN  
*Director of the United States Patent and Trademark Office*